United States Patent
Wingeier et al.

(10) Patent No.: US 10,596,373 B2
(45) Date of Patent: *Mar. 24, 2020

(54) METHOD AND SYSTEM FOR PROVIDING ELECTRICAL STIMULATION TO A USER

(71) Applicant: Halo Neuro, Inc., San Francisco, CA (US)

(72) Inventors: Brett Wingeier, San Francisco, CA (US); Daniel S. Chao, San Francisco, CA (US); Lee von Kraus, San Francisco, CA (US); Amol Sarva, San Francisco, CA (US); Sophia Sanchez, San Francisco, CA (US)

(73) Assignee: Halo Neuro, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/168,607

(22) Filed: Oct. 23, 2018

(65) Prior Publication Data

US 2019/0054298 A1    Feb. 21, 2019

Related U.S. Application Data

(63) Continuation of application No. 15/657,915, filed on Jul. 24, 2017, now Pat. No. 10,143,842, which is a (Continued)

(51) Int. Cl.
*A61N 1/36* (2006.01)
*A61N 1/04* (2006.01)
(Continued)

(52) U.S. Cl.
CPC ........ *A61N 1/36025* (2013.01); *A61B 5/0205* (2013.01); *A61B 5/04001* (2013.01);
(Continued)

(58) Field of Classification Search
CPC ... A61N 1/05; A61N 1/36; A61N 2/00; A61N 1/08; A61N 1/04; A61B 5/16; A61B 5/00; A61B 5/0205; A61B 5/04
(Continued)

(56) References Cited

U.S. PATENT DOCUMENTS 3,472,233 A    10/1969  Sarbacher
4,928,696 A    5/1990   Henderson et al.
(Continued)

FOREIGN PATENT DOCUMENTS

EP    2449961 A1    5/2012
JP    2010152731 A  7/2010
(Continued)

OTHER PUBLICATIONS

US 8,919,831 B2, 12/2014, Tateishi et al. (withdrawn)

*Primary Examiner* — Carl H Layno
*Assistant Examiner* — Jon Eric C Morales
(74) *Attorney, Agent, or Firm* — Jeffrey Schox; Caitlin Ploch

(57) ABSTRACT

A method for providing electrical stimulation to a user as a user performs a set of tasks during a time window, the method comprising: providing an electrical stimulation treatment, characterized by a stimulation parameter and a set of portions, to a brain region of the user in association with the time window; for each task of the set of tasks: receiving a signal stream characterizing a neurological state of the user; from the signal stream, identifying a neurological signature characterizing the neurological state associated with the task; and modulating the electrical stimulation treatment provided to the brain region of the user based upon the neurological signature, wherein modulating comprises delivering a portion of the set of portions of the electrical stimulation treatment to the brain region of the user, while (Continued)

maintaining an aggregate amount of the stimulation parameter of the treatment provided during the time window below a maximum limit.

19 Claims, 5 Drawing Sheets

Related U.S. Application Data continuation of application No. 15/295,008, filed on Oct. 17, 2016, now Pat. No. 9,802,042, which is a continuation of application No. 15/250,160, filed on Aug. 29, 2016, now Pat. No. 9,757,561, which is a continuation of application No. 14/470,747, filed on Aug. 27, 2014, now Pat. No. 9,630,005.

(60) Provisional application No. 61/870,678, filed on Aug. 27, 2013, provisional application No. 61/870,680, filed on Aug. 27, 2013, provisional application No. 61/870,682, filed on Aug. 27, 2013, provisional application No. 61/870,684, filed on Aug. 27, 2013, provisional application No. 61/874,461, filed on Sep. 6, 2013, provisional application No. 61/889,169, filed on Oct. 10, 2013.

(51) Int. Cl.
*A61B 5/00* (2006.01)
*A61B 5/0205* (2006.01)
*A61B 5/04* (2006.01)
*A61N 1/08* (2006.01)
*A61N 2/00* (2006.01)
*A61B 5/0476* (2006.01)
*A61N 1/05* (2006.01)
*A61B 5/0488* (2006.01)
*A61B 5/0496* (2006.01)
*A61B 5/053* (2006.01)

(52) U.S. Cl.
CPC .......... *A61B 5/4064* (2013.01); *A61B 5/4076* (2013.01); *A61B 5/4836* (2013.01); *A61N 1/0456* (2013.01); *A61N 1/08* (2013.01); *A61N 2/006* (2013.01); *A61B 5/0476* (2013.01); *A61B 5/0488* (2013.01); *A61B 5/0496* (2013.01); *A61B 5/0533* (2013.01); *A61N 1/0526* (2013.01); *A61N 1/36082* (2013.01); *A61N 1/36103* (2013.01)

(58) Field of Classification Search
USPC .......................................................... 600/13
See application file for complete search history.

(56) References Cited

U.S. PATENT DOCUMENTS

| | | |
|---|---|---|
| 4,967,038 A | 10/1990 | Gevins et al. |
| 4,977,895 A | 12/1990 | Tannenbaum |
| 5,058,605 A | 10/1991 | Slovak |
| 5,087,242 A | 2/1992 | Petelenz et al. |
| 5,137,817 A | 8/1992 | Busta et al. |
| 5,250,023 A | 10/1993 | Lee et al. |
| 5,387,231 A | 2/1995 | Sporer |
| 5,622,168 A | 4/1997 | Keusch et al. |
| 6,077,237 A | 6/2000 | Campbell et al. |
| 6,263,226 B1 | 7/2001 | Axelgaard et al. |
| 6,379,324 B1 | 4/2002 | Gartstein et al. |
| 6,406,811 B1 | 6/2002 | Hall et al. |
| 6,480,743 B1 | 11/2002 | Kirkpatrick et al. |
| 6,505,079 B1 | 1/2003 | Foster et al. |
| 6,510,333 B1 | 1/2003 | Licata et al. |
| 7,024,247 B2 | 4/2006 | Gliner et al. |
| 7,551,952 B2 | 6/2009 | Gevins et al. |
| 7,610,095 B2 | 10/2009 | Naisberg |
| 7,813,802 B2 | 10/2010 | Tcheng et al. |
| 7,818,515 B1 | 10/2010 | Umbehocker et al. |
| 7,828,947 B2 | 11/2010 | Oki et al. |
| 7,877,146 B2 | 1/2011 | Ansarinia et al. |
| 7,894,905 B2 | 2/2011 | John et al. |
| 7,966,073 B2 | 6/2011 | Pless et al. |
| 7,988,917 B2 | 8/2011 | Roesicke et al. |
| 8,116,875 B2 | 2/2012 | Osypka et al. |
| 8,121,694 B2 | 2/2012 | Molnar et al. |
| 8,195,174 B2 | 6/2012 | Lee et al. |
| 8,239,030 B1 | 8/2012 | Hagedorn et al. |
| 8,290,596 B2 | 10/2012 | Wei et al. |
| 8,301,265 B2 | 10/2012 | Starkebaum |
| 8,349,554 B2 | 1/2013 | Bahrami et al. |
| 8,380,316 B2 | 2/2013 | Hagedorn et al. |
| 8,419,716 B2 | 4/2013 | Weissenrieder-Norlin et al. |
| 8,473,063 B2 | 6/2013 | Gupta et al. |
| 8,554,324 B2 | 10/2013 | Brocke |
| 8,583,237 B2 | 11/2013 | Bedenbaugh |
| 8,591,392 B2 | 11/2013 | Bentwich et al. |
| 8,626,259 B2 | 1/2014 | Besio |
| 8,706,181 B2 | 4/2014 | Stypulkowski et al. |
| 8,795,174 B2 | 8/2014 | Manicka et al. |
| 8,818,515 B2 | 8/2014 | Bikson et al. |
| 8,838,247 B2 | 9/2014 | Hagedorn et al. |
| 8,874,220 B2 | 10/2014 | Draghici et al. |
| 8,874,227 B2 | 10/2014 | Simon et al. |
| 8,880,173 B2 | 11/2014 | Diubaldi et al. |
| 8,903,494 B2 | 12/2014 | Goldwasser et al. |
| 8,938,301 B2 | 1/2015 | Hagedorn |
| 8,979,837 B2 | 3/2015 | De La Rama et al. |
| 8,989,863 B2 | 3/2015 | Osorio |
| 9,002,458 B2 | 4/2015 | Pal et al. |
| 9,080,918 B2 | 7/2015 | Fishel et al. |
| 9,186,505 B2 | 11/2015 | Katsnelson |
| 9,393,430 B2 | 7/2016 | Demers et al. |
| 9,399,126 B2 | 7/2016 | Pal et al. |
| 9,433,774 B2 | 9/2016 | Dar et al. |
| 9,440,063 B2 | 9/2016 | Ho et al. |
| 9,440,070 B2 | 9/2016 | Goldwasser et al. |
| 9,486,618 B2 | 11/2016 | Wingeier et al. |
| 9,517,345 B2 | 12/2016 | Meffin et al. |
| 9,630,005 B2 | 4/2017 | Wingeier et al. |
| 9,643,001 B2 | 5/2017 | Wu et al. |
| 9,731,127 B2 | 8/2017 | Kealey et al. |
| 9,757,561 B2 * | 9/2017 | Wingeier ........... A61N 1/36025 |
| 9,770,204 B2 | 9/2017 | Wu et al. |
| 9,782,585 B2 * | 10/2017 | Wingeier ........... A61N 1/36025 |
| 9,802,042 B2 * | 10/2017 | Wingeier ........... A61N 1/36025 |
| 9,913,973 B2 | 3/2018 | Yanaki |
| 9,981,128 B2 | 5/2018 | Wingeier |
| 10,238,870 B2 | 3/2019 | Pilly et al. |
| 2002/0169485 A1 | 11/2002 | Pless et al. |
| 2004/0019370 A1 | 1/2004 | Gliner et al. |
| 2005/0165460 A1 | 7/2005 | Erfan |
| 2006/0111754 A1 | 5/2006 | Ansarinia et al. |
| 2006/0212093 A1 | 9/2006 | Pless et al. |
| 2006/0229502 A1 | 10/2006 | Pollock et al. |
| 2006/0259094 A1 | 11/2006 | Grinshpoon et al. |
| 2007/0015984 A1 | 1/2007 | Yeo et al. |
| 2007/0023779 A1 | 2/2007 | Hirose et al. |
| 2007/0038265 A1 | 2/2007 | Tcheng et al. |
| 2007/0093706 A1 | 4/2007 | Gevins et al. |
| 2007/0118070 A1 | 5/2007 | Cormier et al. |
| 2007/0213783 A1 | 9/2007 | Pless |
| 2007/0237678 A1 | 10/2007 | Roesicke et al. |
| 2007/0237797 A1 | 10/2007 | Peyman |
| 2007/0238945 A1 | 10/2007 | Delic et al. |
| 2007/0250145 A1 | 10/2007 | Kraus et al. |
| 2008/0004676 A1 | 1/2008 | Osypka et al. |
| 2008/0021520 A1 | 1/2008 | Dietrich |
| 2008/0027345 A1 | 1/2008 | Kumada et al. |
| 2009/0069803 A1 | 3/2009 | Starkebaum |
| 2009/0099627 A1 | 4/2009 | Molnar et al. |
| 2009/0105785 A1 | 4/2009 | Wei et al. |
| 2009/0187159 A1 | 7/2009 | Greger et al. |

(56) References Cited

U.S. PATENT DOCUMENTS

| | | |
|---|---|---|
| 2010/0030129 A1 | 2/2010 | Nitzan et al. |
| 2010/0213070 A1 | 8/2010 | Oki et al. |
| 2010/0268287 A1 | 10/2010 | Celnik |
| 2010/0330589 A1 | 12/2010 | Bahrami et al. |
| 2011/0040291 A1 | 2/2011 | Weissenrieder-Norlin et al. |
| 2011/0054288 A1 | 3/2011 | Besio |
| 2011/0112590 A1* | 5/2011 | Wu .................. A61B 5/4812 607/2 |
| 2011/0118806 A1 | 5/2011 | Pascual-Leone et al. |
| 2011/0276112 A1 | 11/2011 | Simon et al. |
| 2011/0288610 A1 | 11/2011 | Brocke |
| 2011/0319975 A1 | 12/2011 | Ho et al. |
| 2012/0007832 A1 | 1/2012 | Lee et al. |
| 2012/0065699 A1 | 3/2012 | Bedenbaugh |
| 2012/0071947 A1 | 3/2012 | Gupta et al. |
| 2012/0078323 A1 | 3/2012 | Osorio |
| 2012/0184894 A1 | 7/2012 | Imran et al. |
| 2012/0191157 A1 | 7/2012 | Stypulkowski et al. |
| 2012/0226127 A1 | 9/2012 | Asjes et al. |
| 2012/0271377 A1 | 10/2012 | Hagedorn et al. |
| 2012/0289869 A1 | 11/2012 | Tyler |
| 2013/0085347 A1 | 4/2013 | Manicka et al. |
| 2013/0113059 A1 | 5/2013 | Song et al. |
| 2013/0184779 A1 | 7/2013 | Bikson et al. |
| 2013/0204315 A1 | 8/2013 | Wongsarnpigoon et al. |
| 2013/0261706 A1 | 10/2013 | Mirro et al. |
| 2013/0281759 A1 | 10/2013 | Hagedorn et al. |
| 2014/0069212 A1 | 3/2014 | Fishel et al. |
| 2014/0148872 A1 | 5/2014 | Goldwasser et al. |
| 2014/0172041 A1 | 6/2014 | Draghici et al. |
| 2014/0277324 A1 | 9/2014 | Diubaldi et al. |
| 2014/0316505 A1 | 10/2014 | Yanaki |
| 2014/0350431 A1 | 11/2014 | Hagedorn |
| 2015/0005841 A1 | 1/2015 | Pal et al. |
| 2015/0065838 A1 | 3/2015 | Wingeier et al. |
| 2015/0066104 A1 | 3/2015 | Wingeier et al. |
| 2015/0088224 A1 | 3/2015 | Goldwasser et al. |
| 2015/0238759 A1 | 8/2015 | Katsnelson |
| 2015/0238762 A1 | 8/2015 | Pal et al. |
| 2015/0328467 A1 | 11/2015 | Demers et al. |
| 2015/0335877 A1 | 11/2015 | Jeffery et al. |
| 2015/0352357 A1 | 12/2015 | Wei et al. |
| 2015/0352364 A1 | 12/2015 | Meffin et al. |
| 2015/0360027 A1 | 12/2015 | Bachinski et al. |
| 2015/0374971 A1 | 12/2015 | Dar et al. |
| 2015/0375007 A1 | 12/2015 | Takeuchi et al. |
| 2016/0017558 A1 | 1/2016 | French |
| 2016/0022981 A1 | 1/2016 | Wingeier et al. |
| 2016/0175589 A1 | 6/2016 | Wingeier |
| 2016/0184585 A1 | 6/2016 | Kealey et al. |
| 2016/0256105 A1 | 9/2016 | Boyle et al. |
| 2016/0303362 A1 | 10/2016 | Wu et al. |
| 2016/0346530 A1 | 12/2016 | Jeffery et al. |
| 2016/0360990 A1 | 12/2016 | Altshuler et al. |
| 2016/0361541 A1 | 12/2016 | Wingeier et al. |
| 2016/0366507 A1 | 12/2016 | Hou et al. |
| 2017/0021158 A1 | 1/2017 | Wingeier et al. |
| 2017/0224978 A1 | 8/2017 | Lee |
| 2017/0224990 A1 | 8/2017 | Goldwasser et al. |
| 2017/0361096 A1 | 12/2017 | Wingeier |
| 2017/0368344 A1 | 12/2017 | Ironi et al. |
| 2018/0021565 A1 | 1/2018 | Dar et al. |

FOREIGN PATENT DOCUMENTS

| | | |
|---|---|---|
| KR | 20150088224 A | 7/2015 |
| KR | 101685124 B1 | 12/2016 |
| KR | 20170021158 A | 2/2017 |
| KR | 20170028197 A | 3/2017 |
| KR | 20180021565 A | 3/2018 |
| WO | 2013113059 A | 3/1871 |
| WO | 2008048471 A2 | 4/2008 |
| WO | 2009134763 A1 | 11/2009 |
| WO | 2013004763 A1 | 1/2013 |
| WO | 2013113059 A1 | 8/2013 |

* cited by examiner

METHOD AND SYSTEM FOR PROVIDING ELECTRICAL STIMULATION TO A USER

CROSS-REFERENCE TO RELATED APPLICATIONS

This application is a continuation of U.S. patent application Ser. No. 15/657,915, filed 24 Jul. 2017, is now U.S. patent Ser. No. 10/143,842, which is a continuation of U.S. patent application Ser. No. 15/295,008, filed 17 Oct. 2016, now issued as U.S. Pat. No. 9,802,042, which is a continuation of U.S. patent application Ser. No. 15/250,160, filed 29 Aug. 2016, now issued as U.S. Pat. No. 9,757,561, which is a continuation of U.S. patent application Ser. No. 14/470,747, filed 27 Aug. 2014, now issued as U.S. Pat. No. 9,630,005, which claims the benefit of U.S. Provisional Application Ser. No. 61/870,678 filed 27 Aug. 2013, U.S. Provisional Application Ser. No. 61/870,680 filed 27 Aug. 2013, U.S. Provisional Application Ser. No. 61/870,682 filed 27 Aug. 2013, U.S. Provisional Application Ser. No. 61/870,684 filed 27 Aug. 2013, U.S. Provisional Application Ser. No. 61/874,461 filed 6 Sep. 2013, and U.S. Provisional Application Ser. No. 61/889,169 filed 10 Oct. 2013, which are each incorporated in its entirety herein by this reference.

TECHNICAL FIELD

This invention relates generally to the neuromodulation field, and more specifically to a new and useful method for providing electrical stimulation to a user.

BACKGROUND

Electrode systems in the neuromodulation field are used to transmit electrical signals to a subject, and can be used to detect or measure signals from the subject. Current electrode systems for electrical stimulation and/or signal detection are, however, insufficient for many reasons including inadequate contact between the subject and the electrode(s) of a system, non-robust contact between the subject and the electrode(s) of a system, subject discomfort while using an electrode system, and/or limited use within multiple electrical simulation or biosignal detection paradigms. Furthermore, methods of providing electrical stimulation are also inadequate for many reasons.

Thus, there is a need in the neuromodulation field for a new and useful method and system for providing electrical stimulation to a user. This invention provides such a new and useful method.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1:
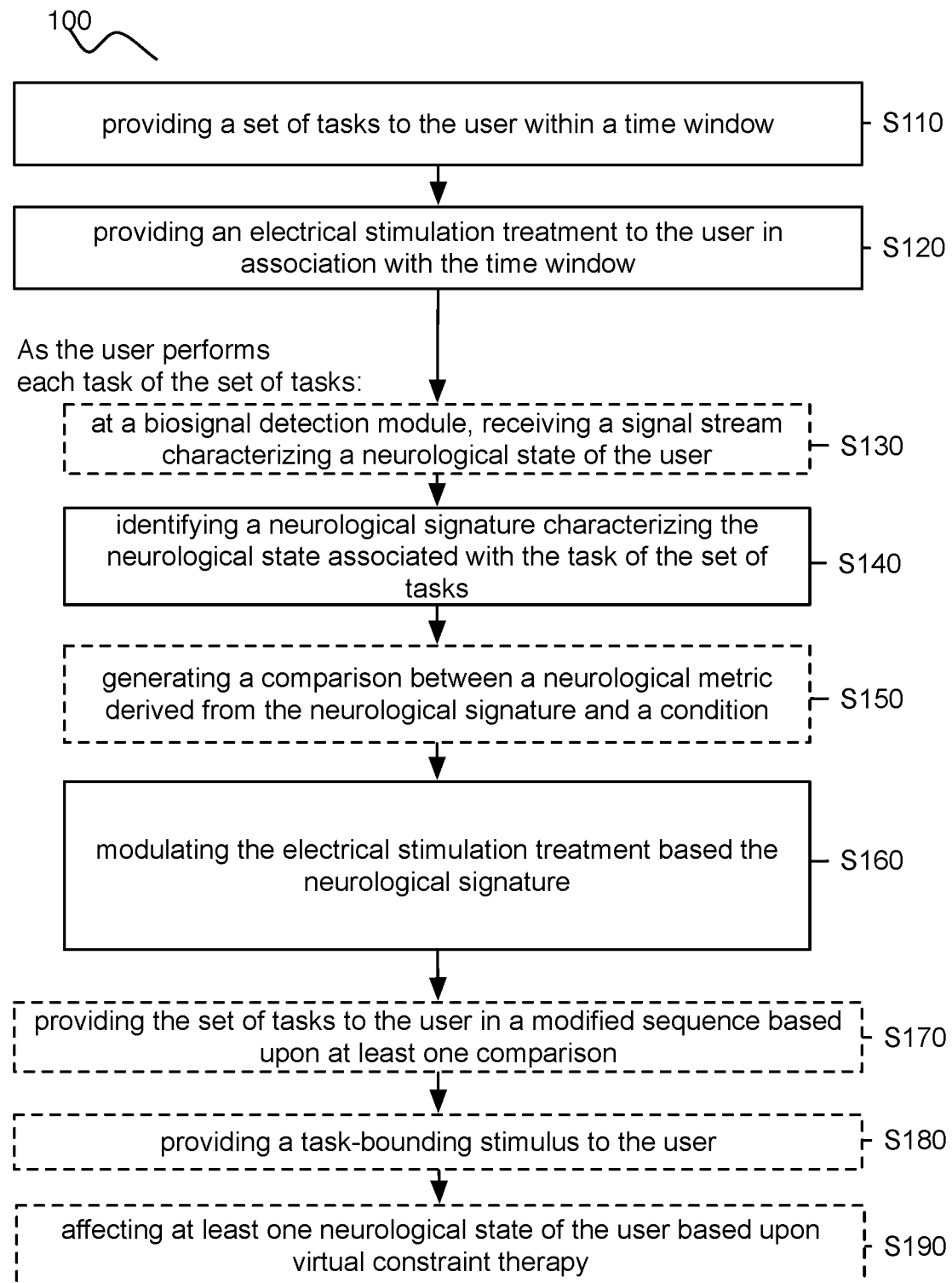
FIG. 1 depicts a schematic of an embodiment of a method for providing electrical stimulation to a user.

As shown in FIG. 1, an embodiment of a method 100 for providing electrical stimulation to a brain region of a user comprises: providing a set of tasks to the user within a time window S110; providing an electrical stimulation treatment to the brain region of the user in association with the time window S120; as the user performs each task of the set of tasks: at a biosignal detection module, receiving a signal stream characterizing a neurological state of the user S130; from the signal stream, identifying a neurological signature characterizing the neurological state S140 associated with the task of the set of tasks; and modulating the electrical stimulation treatment to the user based upon the neurological signature S160, wherein an aggregated parameter of the electrical stimulation treatment provided to the user during the time window does not exceed a maximum limit. The method 100 can additionally comprise: generating a comparison between a neurological metric derived from the neurological signature and a condition S150 for each task in the set of tasks; providing the set of tasks to the user in a modified sequence, based upon at least one neurological signature S170 identified in Block S150; and providing a task-bounding stimulus to the user S180 configured to facilitate consolidation of learned information and/or behavior.

In some variations, the method 100 can substantially omit Block S130, such that modulation of the electrical stimulation treatment in Block S160 is based upon a portion of a task of the set of tasks, or the user's performance of a portion of a task of the set of tasks, without consideration of a neurological state of the user detected by a biosignal detection module. Furthermore, in some variations, the method 100 can substantially omit modulating the electrical stimulation treatment according to a maximum limit constraint, such that modulation is based solely upon a stage of a task and/or a neurological state of the user, without a maximum limit constraint. In still other variations, as described in Section 1.2 below, the method 100 can entirely omit provision of electrical stimulation to the user relative to a set of provided tasks, such that provision and/or modulation of an electrical stimulation treatment is primarily based upon a detected neurological state of the user.

The method 100 functions to strategically control provision of an electrical stimulation treatment delivered to a user as the user performs a set of tasks, wherein the electrical stimulation treatment is provided within specified treatment limits (e.g., for safety, in consideration of maximizing efficacy of the electrical stimulation treatment, etc.). However, the method 100 can additionally or alternatively function to increase an effect of an electrical stimulation treatment provided to the user by modulating the treatment according to a specific stage of a task and/or a neurological state of the user, without a maximum limit constraint. The method 100 can further optimize provision of a limited amount of electrical stimulation to the user, such that the user only receives electrical stimulation when an actual or anticipated neurological state of the user could be improved by receipt of electrical stimulation. In some variations, the method can be used to rehabilitate users diagnosed with neurological pathologies and/or users with neurological conditions that can be improved or treated by electrical stimulation. As such, the method 100 can be used to facilitate management of the user's neurological condition by reversing damage resulting from the neurological condition, halting damage resulting from the neurological condition, and/or by enabling the user to cope with the neurological condition. In other variations, the method 100 can be used to improve a neurological state of a user as the user performs a task of interest, in order to enhance cognitive ability (e.g., mathematical ability), learning (e.g., language learning, speech learning), memory (e.g., working memory, declarative memory), motor ability (e.g., dexterity, coordination), focus, attention, and/or creativity. Thus, the user can be someone who is diagnosed or undiagnosed with a neurological condition. In some specific applications, the method 100 can be used to increase neural plasticity in stroke patients during rehabilitation, to improve the efficacy of therapy sessions for patients with paralyzing neurological disorders, and/or to increase neural plasticity in elderly users.

Preferably, at least a portion of the method 100 is configured to be implemented for a user who is outside of a clinical (e.g., hospital) or research (e.g., laboratory) setting, such that the user can be in a non-contrived environment as he or she is performing the set of tasks and receiving the electrical stimulation treatment. As such, the method 100 is preferably implemented in part by a system 400, described in further detail in Section 2 below, that is portable and comfortably worn by the patient as the patient performs the set of tasks in his/her daily life. Additionally or alternatively, the method 100 can be implemented in an entirely clinical or research setting, such as a physical therapy clinic.

Block S110 recites: providing a set of tasks to the user within a time window, which functions to guide the user through various activities that can operate in coordination with electrical stimulation to have a positive effect on the user's wellbeing. The set of tasks preferably comprises cognitive tasks, and can additionally comprise tasks involving motor functions and/or speech functions of the user. Additionally, the set of tasks is preferably configured to enhance neural plasticity; as such, the set of tasks can comprise games inducing a high level of emotional involvement (e.g., interpersonal emotional content, intrapersonal emotional content), which can enhance neural plasticity. In some variations, the set of tasks can be configured to enhance training for mental activities (e.g., test preparation) and/or physical activities (e.g., athletic activities). In other variations, the set of tasks can be configured to facilitate cognitive therapy or other psychotherapy. In still other variations, the set of tasks can comprise media configured to produce a psychological effect (e.g., desensitization, craving, affective response) in the user. However, the set of tasks can additionally or alternatively be configured to improve other characteristics of the user's nervous system or evoke other desired neurological or psychological effects.

Each task in the set of tasks preferably defines one or more stages of activity (e.g., portions of a task, periods of a task with greater difficulty, periods of a task with lesser difficulty, a period of a task during which an activity is undertaken by the user as opposed to resting periods, practice periods, or periods of instruction provision). The stage(s) can be one or more delivered stage(s) (e.g., if a task is being deterministically delivered by a computing module or a trainer), and/or can be one or more stage(s) governed by the user (e.g., if a task is done at the user's leisure). As such, the set of tasks can comprise multiple tasks, each with multiple stages of activity or a single stage of activity, or can alternatively comprise a single task with multiple stages of activity or a single stage of activity. As such, in examples, the set of tasks can comprise a single task with various parts, stages, and/or time-varying characteristics.

In one variation, the set of tasks provided in Block S110 comprise cognitive games configured to mentally engage a user with a neurological disorder, in order to facilitate improvement in the user's condition. In another variation, the set of tasks provided in Block S110 comprises cognitive games configured to mentally engage a user without a neurological disorder, in order to facilitate enhancement of the user's cognitive abilities. In yet another variation, the set of tasks provided in Block S110 comprises cognitive-motor games configured for a user with a neuromuscular disorder, in order to facilitate improvement in the user's neuromuscular state. In still another variation, the set of tasks provided in Block S110 comprises cognitive-motor games configured for a user without a neuromuscular disorder, in order to facilitate enhancement of the user's neuromuscular abilities.

In specific applications, the set of tasks can comprise any one or more of: a game with an interpersonal emotional aspect (e.g., a game in which a user must draw several components, which are then aggregated into an image that is transmitted to a loved one); a game which facilitates a communication between a user and a loved one of the user; a game which incorporates faces of family and/or acquaintances of the user; a game which incorporates personalized feedback or reinforcement from relatives and/or friends of the user (e.g., in a pre-recorded manner or in real-time). Additionally or alternatively, the set of tasks can include any one or more of: a game which incorporates mirroring of the body of the user (e.g., a game in which movement of one limb causes apparent movement of the contralateral limb), which can enhance neural plasticity by a "mirror-box effect"; games that incorporate a speech or vocal component for a user with a neurological disorder-related speech impairment or desirous of speech improvement (e.g., a game can record a patient's voice for computer speech processing/scoring); games that involve motion of the user's body or a portion of the user's body (e.g., finger strokes, finger tapping, moving objects, etc.) for a user with a neuromuscular disorder or a user desirous of motor improvement, and any other suitable game configured to improve a user's neuromuscular or neurological-speech ability or reduce a user's impairment in these areas. The set of tasks can, however, include any other suitable games or tasks. For instance, in some variations, the set of tasks can include tasks that the user performs regularly (e.g., daily, weekly), within his or her natural environment, such that the method 100 can facilitate tracking of progress in the user's performance of regularly encountered tasks. In examples, such tasks can include tasks related to motor skills (e.g., walking, running, lifting) and speech (e.g., talking on a phone).

In Block S110, each task in the set of tasks can be performed by the user over a duration of seconds, minutes, hours, days, months, or years. Furthermore, the set of tasks is preferably provided such that there is a brief resting or transition period (e.g., several seconds or one minute) between tasks of the set of tasks. The resting or transition period following a task can be constant across all tasks of the set of tasks, or can vary based upon characteristics of the task preceding or following the resting or transition period. In some variations, the resting or transition period can further be governed based upon an input from the user, or can be governed by an overseeing entity (e.g., electronic entity, physical therapist, caretaker of the user). Furthermore, the resting or transition period can be used to provide instruction to the user, used to initialize a subsequent task of the set of tasks, or used in any other suitable manner. In other variations, however, the set of tasks can alternatively be provided to the user such that at least one task of the set of tasks is provided without a following resting or transition period, or such that at least one task of the set of tasks is followed by a task intended to produce a neurological state or effect different from that produced by previous task. Additionally, the time window over which the set of tasks is provided to the user can comprise a time window spanning a period of seconds, a period of minutes, a period of days, a period of months, or a period of years. In a specific example, a task of the set of tasks is configured to be performed by the user over a duration of 10 minutes, followed by a resting period of 1 minute, such that the window of time over which the set of tasks is provided spans a duration of the number of tasks provided multiplied by 11 minutes.

In Block S110, the set of tasks is preferably presented at a task-provision module including a user interface of an application executing on an electronic device (e.g., mobile device, tablet device, personal computer, etc.) of the user; however, the set of tasks can additionally or alternatively be presented to the user using, at least in part, a non-electronic format. In some variations, the set of tasks can additionally or alternatively be provided by a health care professional or other caretaker associated with the user. In one example, the set of tasks can be presented through an application executing on a tablet device of the user, wherein the sensors of the tablet device are used to detect performance of the set of tasks by the user. In the example, a touch screen of the tablet device can be used to detect performance of finger stroking in a task configured to rehabilitate a stroke-affected hand of a user, an accelerometer of the tablet device can be used to sense vibration indicative of finger tapping in a task configured to rehabilitate the stroke-affected hand of the user, and a camera of the tablet device can be used to capture physical movement of objects performed by the user with a stroke-affected hand. In the example, feedback can additionally be provided using audio, visual, and/or haptic modules of the tablet device, in order to indicate successful and/or unsuccessful performance of any task. In relation to a set of tasks including tasks that the user regularly performs in his/her natural environment, one or more sensors of the electronic device can further facilitate automatic detection of performance of a task of the set of tasks. For instance, an accelerometer of the electronic device can facilitate detection of motion (e.g., walking) by the user, and an audio sensor of the electronic device can facilitate detection of speech by the user, which can be used to guide provision of stimulation (e.g., stimulation provided to the lower extremity motor cortex, stimulation provided to Broca's area) at appropriate times in subsequent blocks of the method 100. In other examples, the set of tasks can additionally or alternatively be provided to the user by a physical therapist (or any other suitable human entity) associated with the user.

Block S120 recites: providing an electrical stimulation treatment to the user in association with the time window, and functions to improve a neurological state of the user in association with performance of the set of tasks provided to the user in Block S110. In Block S120, the electrical stimulation treatment is preferably provided to the user at least one of within the time window and proximal in time to the time window, such that the electrical stimulation treatment is associated with provision of at least one task of the set of tasks given to the user in variations of Block S110. As such, and in relation to Block S110, a task of the set of tasks can comprise one or more of an initial resting period and a transition period between adjacent tasks of the set of tasks, such that the electrical stimulation treatment of Block S120 can be provided outside of, but proximal in time to the time window, in relation to the set of tasks (i.e., stimulation can be provided during a period prior to or after performance of the set of tasks), and can additionally or alternatively be provided proximal in time to one or more tasks of the set of tasks.

The electrical stimulation treatment provided in Block S120 preferably increases neural plasticity in the user and in some variations, can additionally or alternatively induce a physiological response that benefits the user. Preferably, the electrical stimulation treatment provided in Block S120 is also configured to minimize effects of metaplastic mechanisms that produce a rebound effect after plasticity is induced or elevated within the user's neurological functions for a period of time. For instance, stimulation that is protracted and/or of an extended duration of time can induce rebounding due to homeostatic mechanisms, which can reduce neural plasticity. However, the electrical stimulation treatment provided in Block S120 can alternatively be configured to have any other suitable effect in relation to metaplastic mechanisms. For instance, some variations of Block S120 can include provision of portions of electrical stimulation that are intended to induce homeostatic mechanisms interspersed between portions of electrical stimulation intended to induce neural plasticity. Block S120 is preferably performed at an electrical stimulation module coupled to a head region of the user, such as the electrical stimulation module described in Section 2 below, in order to facilitate stimulation of a brain region of the user; however, Block S120 can alternatively be performed using any other suitable electrical stimulation module.

In Block S120, the electrical stimulation treatment is preferably transcranial electrical stimulation (TES) configured to stimulate a brain region of the user in the form of at least one of: transcranial direct current stimulation (tDCS), transcranial alternating current stimulation (tACS), transcranial magnetic stimulation (TMS), transcranial random noise stimulation (tRNS), and/or transcranial variable frequency stimulation (tVFS). In these variations, the TES can be provided using one or more electrodes, such as an anodal or cathodal electrode, positioned at a desired location on the user's skull and an electrode of the opposite polarity, such as a cathodal or anodal electrode, positioned on or off of the user's skull, or using any other suitable number of electrodes in any other suitable location. For instance, in some variations, Block S120 can include positioning a first electrode at a first region of the user's head (e.g., C3, C4, F3, F4, Fz, or FCz, or between 0 and 2 cm rostral to C3 or C4), and a second electrode at a second region of the user's head (e.g., the left or right supraorbital area, C3, C4, F3, F4, Fz, or FCz, or between 0 and 2 cm rostral to C3 or C4), or another region of the user's body (e.g., the shoulder, back, or pectoral region).

In variations of Block S120, the electrical stimulation treatment can additionally or alternatively comprise any other form of electrical stimulation configured to stimulate any other suitable region of the user's body, with any suitable penetration depth, and/or any suitable target tissue structure (e.g., neural, musculoskeletal). In one such variation, the electrical stimulation can additionally or alternatively comprise peripheral nerve stimulation (PNS), which provides stimulation of the peripheral nerves of an extremity (e.g., a hand of the user) and can increase neural plasticity. In some applications, PNS and other stimulation treatments can interact synergistically with TES (e.g., tDCS) and potentiate effects of TES stimulation. Similar to the TES treatment, the PNS can be characterized by a set of treatment parameters (e.g., duration, intensity, amplitude, frequency, waveform, modulation, etc). Furthermore, the PNS can be provided using electrodes placed near peripheral nerves of the user at an extremity (e.g., limb, hand, wrist, leg, ankle, etc.) of the user. In variations of Block S120 comprising provision of both TES and PNS, the electrical stimulation treatment can be characterized by a ratio of any suitable parameter of the TES to any suitable parameter of the PNS (e.g., amplitude of TES:PNS, duty cycle of TES:PNS, etc.). Thus, in variations, the electrical stimulation treatment can thus comprise multiple forms (e.g., not limited to TES and PNS), wherein the forms can be performed simultaneously and/or in sequence. Similarly, the electrical stimulation treatment can be characterized by any suitable ratio of parameters of different forms of treatment.

The electrical stimulation treatment provided in Block S120 is preferably characterized by at least one stimulation parameter and a set of portions. The stimulation parameter preferably comprises one or more of: a form (e.g., direct current, direct current with a superimposed non-direct current component, alternating current with one or more frequency components, band-limited, time-varying, etc.), a current or voltage amplitude, a stimulation duration, a stimulation duty cycle, a stimulation localization/current path (e.g., the location and anode/cathode configuration of electrodes through which stimulation is delivered) of the electrical stimulation treatment, a waveform of the stimulation (e.g., direct current alone, random noise stimulation, variable frequency stimulation, etc.), an on/off-status of the stimulation, a polarity of the stimulation (e.g., anodal, cathodal) and any other suitable stimulation parameter. As such, the stimulation parameter is preferably configured to be modulated, as described in more detail with regard to Block S160 below. The stimulation parameter can, however, be characterized by any other suitable combination of parameters. The set of portions of the electrical stimulation treatment preferably comprises periods of active stimulation (e.g., an on-status of stimulation, wherein the on-status can be associated with any suitable polarity of stimulation) separated by one or more periods of non-active stimulation (e.g., an off-status of stimulation). In variations, the periods of active stimulation can be substantially identical (e.g., in stimulation parameter(s), in duration, in polarity, in magnitude, etc.) or non-identical. Similarly, the periods of non-active stimulation can be substantially identical in duration, or non-identical in duration. In examples, Block S120 includes providing at least two periods of active stimulation separated by one period of non-active stimulation; however, other variations of Block S120 can include provision of any suitable number of active periods of stimulation and any suitable number of non-active periods of stimulation.

Figure 2A:
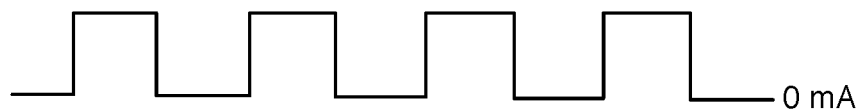
FIGS. 2A-2E depict variations of waveforms of an electrical stimulation treatment in an embodiment of a method for providing electrical stimulation to a user.
Figure 2B:
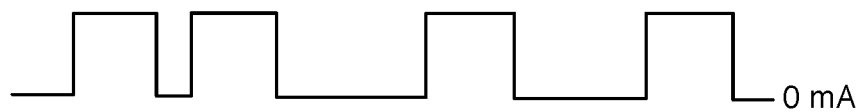
Figure 2C:
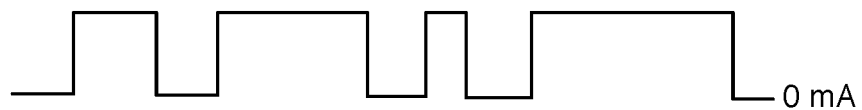
Figure 2D:
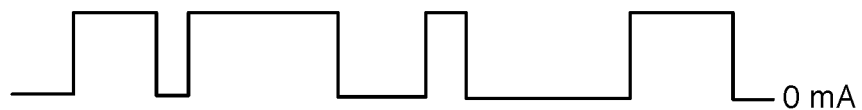
Figure 2E:
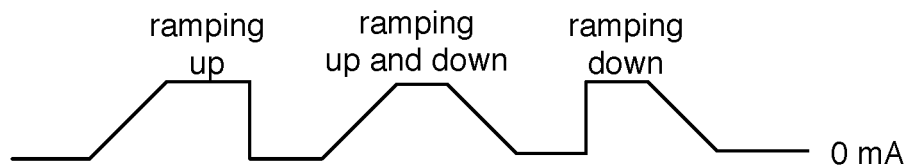

In Block S120, the stimulation waveform(s) provided as part of the electrical stimulation treatment preferably includes a monophasic waveform; however, the stimulation waveforms(s) can additionally or alternatively include one or more of: a symmetrical biphasic waveform, an asymmetrical biphasic waveform, and any other suitable waveform type. In a first example of a monophasic waveform, a waveform can include DC stimulation with portions of equal duration and resting intervals of equal duration, as shown in FIG. 2A. In a second example of a monophasic waveform, a waveform can include DC stimulation with portions of equal duration and resting intervals of non-equal (e.g., random) duration, as shown in FIG. 2B. In a third example of a monophasic waveform, a waveform can include DC stimulation with portions of non-equal (e.g., random) duration and resting intervals of equal duration, as shown in FIG. 2C. In a fourth example of a monophasic waveform, a waveform can include DC stimulation with portions of non-equal (e.g., random) duration resting intervals of non-equal (e.g., random) duration, as shown in FIG. 2D. In any of the above examples, initiation and/or termination of a waveform can include a ramping up and/or a ramping down in current amplitude, as shown in FIG. 2E. Variations of the waveform(s) of the electrical stimulation treatment can additionally or alternatively include any other suitable waveform(s).

Block S130 recites: as the user performs each task of the set of tasks: at a biosignal detection module, receiving a signal stream characterizing a neurological state of the user. Block S130 functions to enable detection and characterization of a neurological state of the user as the user performs each task in the set of tasks, so that the electrical stimulation treatment can be modulated based upon the task-related neurological states, as described in further detail with respect to Block S160 below. However, in some variations, the method 100 can substantially omit Block S130, such that modulation of the electrical stimulation treatment in Block S160 is based solely upon a stage of a task of the set of tasks, or the user's performance of a stage of a task of the set of tasks, without consideration of a neurological state of the user detected by a biosignal detection module. In variations wherein modulation of the electrical stimulation treatment in Block S160 is based upon a neurological state of the user detected by a biosignal module, the biosignal module can be an embodiment of the biosignal detection module described in Section 2 below, or can alternatively be any other suitable biosignal detection module. The signal stream received in Block S130 preferably comprises bioelectrical signals, including electroencephalograph (EEG) signals, which can be reflective of cognitive and/or mental states of the user. The bioelectrical signals can additionally or alternatively include any one or more of: electrooculography (EOG) signals, galvanic skin response (GSR) signals, electromyelography (EMG) signals, and any other suitable bioelectrical signals indicative of a cognitive state and/or physiological state of the user.

Furthermore, in variations of the method 100 including Block S130, Block S130 can comprise receiving other biosignals, at the biosignal detection module, including signals related to cerebral blood flow (CBF), optical signals (e.g., eye movement, body movement), mechanical signals (e.g., mechanomyographs), chemical signals (e.g., blood oxygenation, blood glucose level, or neurotransmitter level), signals indicative of respiratory rate, and/or any other signals obtained from or related to biological tissue, biological processes, or mental processes of the user. Furthermore, any suitable signals related to the user's environment can also be received in Block S130, such as signals related to temperature and/or location (e.g., global positioning signals), or signals reported by the user or other entity (e.g., by a survey). In some variations, signals received in Block S130 can thus provide a comprehensive characterization of the user's cognitive, physiological, and/or environmental state based upon multiple sensor types, in order to provide a basis for modulation of electrical stimulation based upon user neurological state. In other variations, the set of signals received in Block S130 can provide a simpler characterization of the user's cognitive state, based solely upon a single signal type (e.g., EEG signals) received at a biosignal detection module. Again, in some variations, the method 100 can substantially omit receiving signals at a biosignal detection module, such that modulation is not based upon detected biosignals from the user.

In Block S130, the signal stream preferably includes signals from multiple sensor channels, wherein each sensor channel is associated with a sensor located at a desired location or region of the user. In one example, each sensor channel is associated with a region of the user's scalp, in order to receive signals associated with channels paired with one or more of the user's frontal lobe, parietal lobe, occipital lobe, and temporal lobe. In another example, each sensor channel is associated with a region of cortex (e.g., prefrontal cortex, premotor cortex, primary motor cortex, sensory cortex) of the user's brain. As such, a neurological state can be characterized by signal profiles from a single or multiple brain regions. The set of signals can alternatively comprise a single signal (e.g., from a single channel or as a composite of multiple multiplexed channels), or a plurality of composite signals, each of which is a composite of multiple multiplexed channels. In one example, the set of signals can comprise a channel of multiplexed signals from one region of the user, and another channel of multiplexed signals from another region of the user. The set of signals can also be a compressed, filtered, conditioned, amplified, or otherwise processed version of raw signals from one or more sensors. However, the set of signals can alternatively be of any other suitable form or format.

Preferably, the signal stream characterizing the neurological state(s) of the user (e.g., as associated with each task) are received continuously as the user performs each task in the set of tasks in Block S130; however, the signal stream can additionally or alternatively be received intermittently and/or when prompted by the user or other entity. For example, signals of the signal stream can be received at one or more time points during the user's performance of each task in the set of tasks (e.g., in sequence with key events during each task in the set of tasks, at time points relative to different stages of a task). Additionally, signals of the signal stream are preferably received substantially in real time, in order to facilitate real time or near-real time identification of neurological signatures, generation of neurological metrics, and/or generation of comparisons between metrics and threshold conditions in Blocks S140 and S150, respectively, and/or real time or near-real time stimulation modulation in Block S160. However, the set of signals can alternatively be received with any suitable temporal delay, or in any other suitable manner. For example, in variations wherein the user's neurological states undergo a cyclic pattern, the set of signals can be received with a temporal delay that is synchronized with the cyclic pattern, such that a set of signals characterizing one cycle is received in synchronization with another cycle being experienced by the user.

In one example, the signal stream received in Block S130 can be indicative of neural plasticity, and can include signals indicative of user attention and/or engagement as the user performs each task set of tasks. The signals indicative of neural plasticity can include eye tracking data (e.g., from an infrared or other image sensor), EOG activity, EEG signals and potentials (e.g., p300 responses, steady state visually evoked potentials), cardiac data (e.g., heart rate, heart rate variability, or ECG), and signals indicative of the user's motion (e.g., finger activity) as the user performs a task. The signals can additionally or alternatively be supplemented with data indicative of the user's performance level, including recent scores on tasks of the set of tasks, and an improvement indicator (e.g., slope of a line fitted to task scores). Additionally, the signals received in the example of Block S130 can be supplemented by data from the user, including demographic (e.g., age, gender, ethnicity, etc.) and pathological (e.g., type of neurological disorder, medication regimen information) data. Furthermore, the signals received in the example of Block S130 can be supplemented by environmental data (e.g., the time of day relative to times wherein the user experiences peaks of engagement, as determined by questionnaires and/or tracking of engagement and attention across a given time period), and performance level data (e.g., most recent scores for each task, slope of improvement for each task, rate of change of improvement for each task, measure of EEG evoked potentials induced by PNS for electrophysiological tracking of sensory map recovery or remapping, etc.) based upon present or past performances of each task in the set of tasks.

Block S140 recites: from the signal stream, identifying a neurological signature quantifying the neurological state associated with the task of the set of tasks, and functions to transform the signal stream received in Block S130 into at least one signature or metric, corresponding to each task in the set of tasks, that is indicative of a state of neural plasticity in the user, and upon which modulation of the electrical stimulation treatment can be based. The neurological signature can be based upon a combination of data generated from multiple biosignal types from Block S130, but can additionally or alternatively be based upon data from a single type of biosignal from Block S130. Furthermore, the neurological signature preferably characterizes a single aspect of the user's neurological state during, prior to, and/or after performance of a task; however, in other variations, the neurological signature can characterize multiple aspects of the user's neurological state (e.g., plasticity state, emotional state, motor-response state, sensation awareness, etc.), and/or Block S140 can include identifying a set of signatures, each signature in the set of signatures characterizing a single aspect of the user's neurological state. In specific examples, the neurological signature(s) can be derived from detection of evoked potentials (e.g., motor evoked potentials, MEPs), and can be related to amplitudes of evoked potentials, frequency of evoked potentials, duration of evoked potential activity, and any other suitable parameter of evoked potentials. However, variations of the specific examples can additionally or alternatively include signatures derived from any other suitable evoked potential (e.g., sensory evoked potential, somatosensory evoked potential, brainstem auditory evoked potential, visual evoked potential, auditory evoked potential, etc.), or any other suitable signature(s). For instance, in Block S140, a time-varying component of task performance (e.g., fluctuations in maximum force in a pinch force test, fluctuations in force provided during a muscle endurance test) that is associated with (e.g., phase-locked with) a similar time-varying component of provided stimulation can be detected in a manner similar to detection of a steady-state evoked response. In this example, an amplitude and phase offset of the time-varying component of task performance can then be used, in subsequent blocks of the method 100, to modulate stimulation parameters (e.g., amplitude, montage, or effective location) in order to identify the stimulation parameter(s) that maximize a desired effect (e.g., with a goal of identifying optimal settings for motor cortex stimulation).

In one variation of Block S140, the neurological signature characterizes the user's neural plasticity state as the user performs a task (or a stage of a task) of the set of tasks, such that Block S140 includes identification of a neurological signature characterizing user plasticity for each task in the set of tasks. In an example of this variation, the neurological signature can be incorporated into a neurological metric calculated based upon a combination of any one or more of: a parameter of detected evoked potentials, eye tracking data (e.g., a parameter characterizing an amount of eye movement in relation to events in a provided task), a correlation between EOG activity and events in a provided task, user responsiveness data as characterized by detected EEG potentials in a provided task (e.g., EEP P300 responses in relation to visually stimulating events, steady state visually evoked potential responses to an ongoing frequency of visually stimulating events in a provided task), other biosignal data (e.g., metrics related to GSR, heart rate, and respiration), time-related user interaction data (e.g., an amount of finger activity while the user performs a given task, length of time during which the user interacts with the task that is over a time required for therapy, etc.), user success data during interaction with the task (e.g., number of errors made, number of attempts made, accuracy, specificity, sensitivity, Matthews correlation coefficient, informedness, markedness), demographic (e.g., age, gender, ethnicity, etc.) and pathological (e.g., type of neurological disorder) data reported by the user or other entity, environmental data (e.g., time of day, temperature, location, etc.), and performance level data (e.g., most recent scores for each task, slope of improvement for each task, rate of change of improvement for each task, measure of EEG evoked potentials induced by PNS for electrophysiological tracking of sensory map recovery, etc.). In other examples of this variation, the user's neurological plasticity state can alternatively be characterized by any other suitable signature/metric based upon any other suitable factor or combination of factors.

Block S140 can additionally or alternatively include predicting an expected neurological state of the user based upon at least one of a task of the set of tasks and a stage of a task of the set of tasks, in particular, for variations of the method 100 omitting Block S130. As such, a neurological signature identified and/or a neurological metric generated in Block S140 can be based solely upon a stage of activity of a task or a task of the set of tasks, and can be reflective of an expected neurological state of the user without using biosignals (i.e., instead relying upon a location within the set of tasks, a location within a task, and/or a location within a stage of activity of a task). The relationship between the expected neurological state of the user and the task or stage of activity can be generated from prior performances of the set of tasks by the user, and/or from performances of the set of tasks by at least one other user. Furthermore, the neurological signature or metric that is used to predict an expected neurological state of the user can be used as a rationale to modulate the electrical stimulation treatment in Block S160.

Identification of the neurological signal(s), in Block S140, from a signal stream received in Block S130 can additionally or alternatively implement a machine learning algorithm. In variations, the machine learning algorithm can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4-5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, independent component analysis, partial least squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. As such, training data can be used to improve detection and identification of neurological signatures, in order to improve provision and modulation of the electrical stimulation treatment relative to identified neurological signatures.

In variations wherein identifying the neurological signature in Block S140 includes generation of a neurological metric, the method 100 can further include Block S150, which recites: generating a comparison between a neurological metric derived from the neurological signature and a condition for each task in the set of tasks. Block SS150 can function to provide a basis for modulating the electrical stimulation treatment in Block S160. Thus, Blocks S130, S140, and/or S150 can collectively function to enable identification of one or more stage(s) of activity for one or more tasks in the set of tasks, for which the electrical stimulation treatment provided in Block S120 should be modulated in Block S160. Again, variations of the method 100 can omit Block S130, such that Blocks S140 and S150 omit incorporation of detected biosignal data in modulation of the electrical stimulation treatment in Block S160. In Block S150, the condition and the comparison can be implemented using a searching algorithm (e.g., grid search, random search, gradient descent) to identify the stage(s) of activity during which modulation should be effected to enhance the user's neurological state (e.g., performance state, attention state, etc.). The condition in Block S150 can indicate that the user should receive a higher degree (e.g., intensity) of electrical stimulation, which would improve the user's neurological state. Additionally or alternatively, the condition in Block S150 can indicate that the user should receive a lower degree (e.g., intensity) of electrical stimulation, which would improve the user's neurological state (e.g., plasticity state, emotional state, motor-response state, sensation awareness, etc.).

In one variation of Block S150, wherein the user's neurological state of interest is related to neural plasticity, the comparison between the neurological metric and the condition can indicate that the user's attentiveness/engagement during the task has placed him or her in a state of high neural plasticity, thus requiring either a lower level of electrical stimulation (e.g., if the user is already in a state known to produce neural plasticity and therefore does not need additional electrical stimulation) or a higher level of electrical stimulation (e.g., if it is desirable to cause periods of maximal plasticity by delivering electrical stimulation when endogenous plasticity is already high). Conversely, the comparison between the neurological metric and the condition can indicate that the user's attentiveness/engagement during the task has placed him or her in a state of low neural plasticity, thus warranting a higher level of electrical stimulation (e.g., if it is desirable to maintain a constant level of plasticity by delivering more stimulation when endogenous plasticity is low) or a lower level of electrical stimulation (e.g., if it is desirable to cause intermittent periods of minimal plasticity). The condition can additionally or alternatively indicate that modulated stimulation should or should not be provided with a delay relative to a stage of activity of a task associated with a neurological state captured in the neurological metric/signature.

The condition can be identical for all tasks of the set of tasks, or alternatively, each task of the set of tasks can have a corresponding condition that may or may not be identical to a condition for another task of the set of tasks. The condition can be based solely upon a stage of activity of the set of tasks (e.g., a timing relative to a task or a stage of activity of the set of tasks), or can comprise a threshold condition. In variations comprising a comparison to a threshold condition, the threshold condition can involve a threshold value or a threshold range of values, including at least one limiting value (e.g., upper limiting value, lower limiting value). As such, generation of the comparison can be performed in a manner that is inclusive of a limiting value, such that the threshold condition is satisfied even if the neurological metric is substantially equivalent to the limiting value of the threshold range of values. Alternatively, generation of the comparison can be performed in a manner that is exclusive of a limiting value, such the threshold condition is not satisfied if the neurological metric is substantially equivalent to the limiting value of the threshold range of values. The comparison between the threshold condition and the neurological metric can, however, be performed in any other suitable manner.

Block S160 recites: modulating the electrical stimulation treatment provided to the user based upon the neurological signature, which functions to increase an effect of the electrical stimulation treatment provided by targeting neurological states/stages of activity of the user wherein the user would receive greater benefit from stimulation or modulation of stimulation. Block S160 can additionally function to decrease habituation of the user's brain to the electrical stimulation treatment, by delivering stimulation that has a temporally varying component, for instance, as provided by the set of portions (e.g., active periods, non-active periods) of the electrical stimulation treatment. Furthermore, Block S160 can additionally function to facilitate desirable long-term effects, such as long-term potentiation (LTP) and long-term depression (LTD), and short-term effects, such as neural depolarization, excitation, hyperpolarization, and inhibition, by delivering electrical stimulation that tends to excite populations of neural cells where excitation is desirable, tends to inhibit populations of neural cells where inhibition is desirable, and/or tends not to affect populations of neural cells where neuromodulation is undesirable.

Modulation in Block S160 preferably comprises delivering a portion (e.g., active period, non-active period) of the set of portions of the electrical stimulation treatment to the brain region of the user, while maintaining an aggregate amount of the stimulation parameter of the electrical stimulation treatment provided to the user during the time window below a maximum limit. Modulation can, however, omit consideration of maintaining an aggregate amount of the stimulation parameter below a maximum limit, and can additionally or alternatively include maintaining any other suitable value of the stimulation parameter above or below any suitable limit. In some variations, modulating in Block S160 can additionally or alternatively comprise increasing a value of a stimulation parameter of the electrical stimulation treatment, decreasing a stimulation parameter, or substantially eliminating stimulation based upon an output of Block S150. In variations, modulation can include increasing excitatory stimulation during specific neurological states/stages of activity identified in Blocks S130-S150, such as periods of greater attention (i.e., in order to potentiate a desirable activity further). In variations, modulation can additionally or alternatively include increasing inhibitory stimulation during specific neurological states/stages of activity identified in Blocks S130-S150, such as periods of greater attention (i.e., in order to inhibit an undesirable activity, such as phobic or craving response). In variations, modulation can additionally or alternatively include decreasing stimulation in order to reserve stimulation for specific neurological states/stages of activity for the user identified in Blocks S130-S150, such as periods of less attention wherein less endogenous plastic activity is occurring.

In some variations of Block S160, modulation of the electrical stimulation treatment can comprise modulation of at least one of the current amplitude, the voltage amplitude, the stimulation duration, the duty cycle, the stimulation localization/current path of the electrical stimulation treatment, a waveform of the stimulation (e.g., direct current alone, random noise stimulation, variable frequency stimulation, etc.), an on/off status of the stimulation, a polarity of the stimulation (e.g., anodal, cathodal), and any other suitable stimulation parameter. In any of these variations, modulation can include a minimum and a maximum parameter limit (e.g., a duration of one portion of stimulation will not exceed a certain amount of time regardless of the length of a stage of activity, or a duration of one portion of stimulation will not be less than a certain amount of time even if a portion of activity is terminated early). Furthermore, modulation can comprise maintaining a first subset of stimulation parameters at desired levels, while modulating a second subset of stimulation parameters (e.g., a first waveform could be applied during a first activity stage of a task and a second waveform could be applied during a non-activity stage of a task while maintaining current amplitude constant, or tVFS stimulation could be applied during a first activity stage and tDCS stimulation could be applied prior to and/or after a second activity stage). Additionally, in variations in which multiple forms of stimulation are provided, modulation can additionally or alternatively comprise modulation of ratios of stimulation parameters for different forms of stimulation (e.g., modulation of a ratio between current amplitude for TES and for PNS). The modulation can be performed in real-time, such that the electrical stimulation provided to the user is modulated in real-time during performance of a task of the set of tasks. Thus, in the examples described above, the user can receive more electrical stimulation in real-time during a period of low engagement and neural plasticity while performing a task, and receive less electrical stimulation in real-time during a period of high engagement and neural plasticity while performing a task. Additionally or alternatively, outputs of Block S130-S150 can be used to modulate electrical stimulation while the user performs a repeat instance of the task at a later timepoint (e.g., if the set of tasks is provided to the user repeatedly during therapy), such that modulation is based upon earlier comparisons between the user's neurological state and conditions such as threshold conditions for each task in the set of tasks.

The modulation of the electrical stimulation treatment in Block S160 can additionally be performed with any suitable timing relative to a stage of activity for each task in the set of tasks. In some variations, providing and/or modulating the electrical stimulation treatment can thus be performed with a certain temporal relationship relative to a task (or stage of activity of a task), and/or a neurological state of the user, based upon an anticipated task (or stage of activity of a task), and/or an anticipated neurological state of the user. As such, provision and/or modulation of the electrical stimulation treatment can be configured to frontload electrical stimulation provided to the user in relation to the set of tasks, backload electrical stimulation provided to the user in relation to the set of tasks, provide stimulation to the user during a task or a stage of activity, provide stimulation to the user prior to a task or a stage of activity, and/or provide stimulation to the user after a task or a stage of activity. Provision of stimulation prior to a task or stage of activity can facilitate future neural changes due to a future execution of a task or activity, and provision of stimulation after a task or a phase of activity can augment consolidation of changes induced by a task or phase of activity. In one example, modulation can include delivering one or more portions of stimulation according to a schedule that front-loads stimulation during a user session of a task/stage of activity to increase a likelihood that a desired amount of stimulation will be provided (e.g., a high minimum duration of stimulation can be provided early in an task and a lower duration of stimulation can be provided later in a task). Furthermore, in this example, modulation can take advantage of "priming" characteristics of stimulation, wherein stimulation provided early in a task is more effective than stimulation provided later in a task, and stimulation has a holdover effect that affects a subsequent task. In another example, stimulation can be modulated only during periods where the user is actively performing a stage of an activity. In yet another example, provision or modulation of stimulation can occur prior to (e.g., 5 minutes prior to) an anticipated task (or stage of activity of a task) such that the stimulation has a lingering effect (e.g., a 5-10 minute carry-over) on the user's neural plasticity, which would increase the effectiveness of the user's therapy, In yet another example, a portion of stimulation can be provided at substantially an intermediate time point (e.g., middle time point) of a task or stage of activity, and in another example, a first portion of stimulation can be provided prior to onset of a stage of activity and a second portion of stimulation can be provided after completion of the stage of activity.

In some variations, multiple forms of electrical stimulation treatment can be temporally synchronized with each other (e.g., simultaneous modulation of both tDCS and PNS provision). In these variations, a first form of electrical stimulation (e.g., tDCS) could facilitate a response by the user to a second form of electrical stimulation (e.g., PNS); furthermore, the second form of electrical stimulation could facilitate a response by the user to the first form of electrical stimulation (e.g., PNS could cause neural cells to fire, increasing a response to tDCS). Additionally or alternatively, in some variations, electrical stimulation treatment can be synchronized with an audio or visual aspect of gameplay in a provided task (e.g., music tempo and/or visual presentation tempo within a provided task can be synchronized with a frequency of a PNS and/or TES parameter to increase treatment effectiveness) in order to enhance neural remapping. In a specific example for a user with tinnitus, audio media can be filtered to eliminate frequencies that are undesirable (i.e., frequencies near a pathologically re-mapped audio frequency, whose cortical representation should not be expanded) for tinnitus treatment.

Furthermore, in some variations of Block S160, the electrical stimulation treatment can be modulated/synchronized with neurological states aside from plasticity related states. For example, electrical stimulation can be provided and modulated according to EEG oscillations, as observed in theta positive and negative states, which can effectively excite or de-excite neurons and promote or inhibit long-term potentiation (LTP). In still other variations, modulation of the electrical stimulation treatment or synchronization of the electrical stimulation treatment with any other factor can be performed with any suitable offset relative to a corresponding task (or stage of activity) of the set of tasks. For instance, stimulation can be modulated a few seconds prior to provision of a corresponding task to increase effectiveness or a few seconds after a stage of activity is identified in order to increase effectiveness). The offset can function to increase effectiveness of a parameter of stimulation that would otherwise have a negligible effect on the user (e.g., 1 Hz sequence of TMS can be enhanced with delivery of anodal tDCS provided with an offset). Modulation prior to an onset of a stage of activity can be performed based upon a prediction of an onset of a neurological state of the user corresponding to the stage of the activity (e.g., based upon an estimate of a duration to complete a task). Modulation prior to an onset of a stage of activity can additionally or alternatively be performed by explicitly requesting notice from the user prior to performing a task, and/or instructing the user to pause action prior to the task in order to modulate stimulation with a desired time-relationship to the task. The electrical stimulation treatment provided can, however, be modulated or synchronized with respect to any other suitable factor in any other suitable manner.

In some applications of the method 100, it may be desirable that an aggregated amount of at least one stimulation parameter of the electrical stimulation treatment (e.g., TES) provided during a time window does not exceed a maximum limit, for example, for safety reasons. As such, a maximum limit for an aggregated value of a stimulation parameter as related to Block S160 can be any one or more of: a maximum dosage (e.g., duration of stimulation, aggregated charge, aggregated charge density etc.) per day, a maximum dosage per shorter unit of time (e.g., minutes, hours), and any other suitable maximum dosage. In one example, a daily dosage of 30 minutes is an acceptable dosage of tDCS, with higher doses increasing chances of skin irritation for the user and/or other side effects. Furthermore, a remaining allowable stimulation can be tracked in relation to the maximum limit as an accumulated amount of stimulation subtracted from a maximum dosage of stimulation. Here, the accumulated dosage can be increased by additional electrical stimulation, and decreased (e.g., according to a logarithmic decay) when stimulation is not occurring. Thus, maximizing an effect of electrical stimulation treatment given a maximum acceptable limit of treatment can significantly benefit a user's recovery/rehabilitation rate. In variations wherein the electrical stimulation treatment includes TES, the maximum limit is preferably a maximum amount of charge or charge density (e.g., determined based upon current amplitude, duration, duty cycle, and electrode path) that can be delivered to the user per unit time (e.g., the time window). Additionally or alternatively, the electrical stimulation provided within the time window can be transmitted and modulated such that at least a minimum amount of stimulation (i.e., defined as an amount below which stimulation has no effect) is always provided to the user within the time window. For example, a minimum duration and/or duty cycle of tDCS can always be provided to the user within the time window so that the electrical stimulation treatment provided to the user always has a measureable effect on the user's neural plasticity. As such, the method 100 enables transmission of a limited amount of electrical stimulation treatment to the user in a manner that automatically provides the user with electrical stimulation when the user needs electrical stimulation the most, and in a manner that has a measureable effect on the user's neurological condition. Again, in some variations, the method 100 can substantially omit modulating the electrical stimulation treatment according to a maximum limit constraint, such that modulation is based solely upon a stage of a task and/or a neurological state of the user, without a maximum limit constraint.

As shown in FIG. 1, the method 100 can additionally comprise Block S110, which recites: providing the set of tasks to the user in a modified sequence in a subsequent time window, based upon at least one identified neurological signature S170 generated in Block S140 and an outcome of modulating the electrical stimulation treatment. Block S170 functions to affect distribution of the electrical stimulation treatment provided, based upon the user's detected neurological state for each task in the set of tasks, which can increase the effectiveness of the electrical stimulation treatment provided. In one variation, involving modulation based upon user attentiveness as an indicator of neural plasticity, more "interesting" tasks can be interleaved with less interesting tasks and provided to the user in this modified sequence, such that the user receives electrical stimulation with cyclic modulations (e.g., modulated upward for the less interesting tasks and modulated downward for the more interesting tasks, modulated upward for 10 minutes and modulated downward for 10 minutes in repeating cycles corresponding to transitions between tasks of the set of tasks), which can increase treatment effectiveness. Furthermore, in this variation, residual effects of electrical stimulation modulated upward during less interesting tasks can carry over to periods in which the user is performing more interesting tasks, to increase effectiveness. In another variation, involving modulation based upon user attentiveness as an indicator of neural plasticity, more "interesting" tasks can be grouped together and less interesting tasks can be grouped together and provided to the user in this modified sequence, such that the user receives at least one consolidated period of electrical stimulation due to the state-based modulation in Block S160. In other variations, the set of tasks, however, can be provided to the user in any other suitable sequence or configuration based upon at least one identified neurological signature/neurological metric generated in Blocks S140-S150.

Also shown in FIG. 1, the method 100 can further comprise Block S180, which recites: providing a task-bounding stimulus to the user. Block S180 functions to facilitate consolidation of learned information and/or behavior resulting from the user's interactions with the set of tasks and the modulated electrical stimulation treatment. Similar to Block S110, the task-bounding stimulus is preferably provided to the user at an application executing on an electronic device of the user; however, the task-bounding stimulus can be provided in any other suitable manner. In some variations, the task-bounding stimulus can be a visual stimulus, and in other variations, the task-bounding stimulus can be configured to stimulate any other sensory pathway (e.g., auditory pathway, olfactory pathway, tactile sensation pathway, etc.) of the user. In an example, after the set of tasks is provided to the user, the task-bounding stimulus can comprise a video of a similar user repeating a task that the user has just performed, which can stimulate mirror neurons and allow consolidation of information learned from the task that the user has just performed. The task-bounding stimulus can, however, include any other suitable stimulus and be provided in any other suitable manner.

Also shown in FIG. 1, the method 100 can further comprise Block S190, which recites: affecting at least one neurological state of the user based upon virtual constraint therapy, in relation to at least one task of the set of tasks provided in Block S110. Similar to Block S120, Block S190 functions to improve a neurological state of the user; however, Block S190 can supplement an effect of electrical stimulation provided in Block S120 and modulated in Block S160 and accelerate neurological remapping in a manner that does not require excess electrical stimulation to be provided to the user. In relation to stroke, which typically affects one side of the body more than the other, virtual constraint therapy can force a stroke patient to use his/her affected limb (or other body portion) by constraining the contralateral, more healthy limb (or other body portion). As such, the virtual constraint therapy preferably includes constraining motion of the user during performance of a task in a beneficial manner (e.g., constraining motion of a contralateral side of a stroke patient, such that the patient is forced to use his/her weaker side during implementation of the method), and can additionally or alternatively comprise any other suitable target of virtual constraint. The virtual constraint therapy provided in Block S190 is preferably facilitated with a sensor subsystem configured to detect motion (e.g., absolute motion, relative motion) of one or more body parts of the user, which can be used to provide feedback to the user in discouraging motion of the body part(s) of the user. In variations, the sensor subsystem can include one or more of: an accelerometer, a gyroscope, a compass, a pressure sensor, a global positioning system, and any other suitable sensor. The virtual constraint therapy can be supplemented with a physical restraint (e.g., sling or mitt configured to constrain motion of a limb), or can alternatively be provided without a physical restraint. Furthermore, the virtual constraint can be reinforced with positive reinforcement and/or negative reinforcement. Additionally, the virtual constraint of Block S190 can be dynamically modulated, such that a virtual "envelope" around a constrained body region of the user can be dynamically varied in size according to the user's progress, by using a sensor subsystem configured to detect motion of the user with an adjustable envelope of detection. In variations, the virtual envelope can be adjusted in real-time by changing thresholds on an amount of allowable movement prior to provision of positive reinforcement and/or negative reinforcement to the user. Dynamic modulation of the virtual constraint thus allows the user to gradually build up an ability for self-restraint of a less affected region of his/her body in order to strengthen an affected body region.

In one example of Block S190, wherein the user's hand is the target of the virtual constraint therapy, a negative sound can be configured to play at a mobile device of the user whenever the user moves his/her virtually constrained hand while performing a task of the set of tasks provided in Block S110. The user is thus incentivized to maintain virtual constraint of his/her hand, which can improve the user's response to rehabilitation. In another example of Block S190, wherein the user's hand is the target of the virtual constraint therapy, points can be deducted from the user whenever the user moves his/her virtually constrained hand during performance of a provided task. Similarly, the user is thus incentivized to maintain virtual constraint of his/her hand, which can improve a response to rehabilitation. In either example, detection of motion of the user can be enabled by use of at least one accelerometer of a system for implementing the method 100. Furthermore, in either example, the accelerometer can be incorporated into an element of the system for providing PNS, or can be a standalone component configured to primarily facilitate the virtual constraint therapy.

Variations of the method 100 can additionally or alternatively include any other suitable blocks or steps configured to facilitate provision of an electrical stimulation treatment for improving or enhancing cognitive functions of a user. Additionally, and as noted above, one embodiment of the method 100 can omit use of detected biosignals, such that provision of portions of the electrical stimulation treatment and modulation of the electrical stimulation treatment are based upon relative timing with a set of provided tasks. Such a method 200 is described further in Section 1.1 below. In another embodiment, the method 100 can omit provision of electrical stimulation to the user relative to a set of provided tasks, such that provision and/or modulation of an electrical stimulation treatment is primarily based upon a detected neurological state of the user. Such a method 300 is described further in Section 1.2 below.

1.1 Method—Intermittent Stimulation Relative to One or More Provided Tasks

Figure 3A:
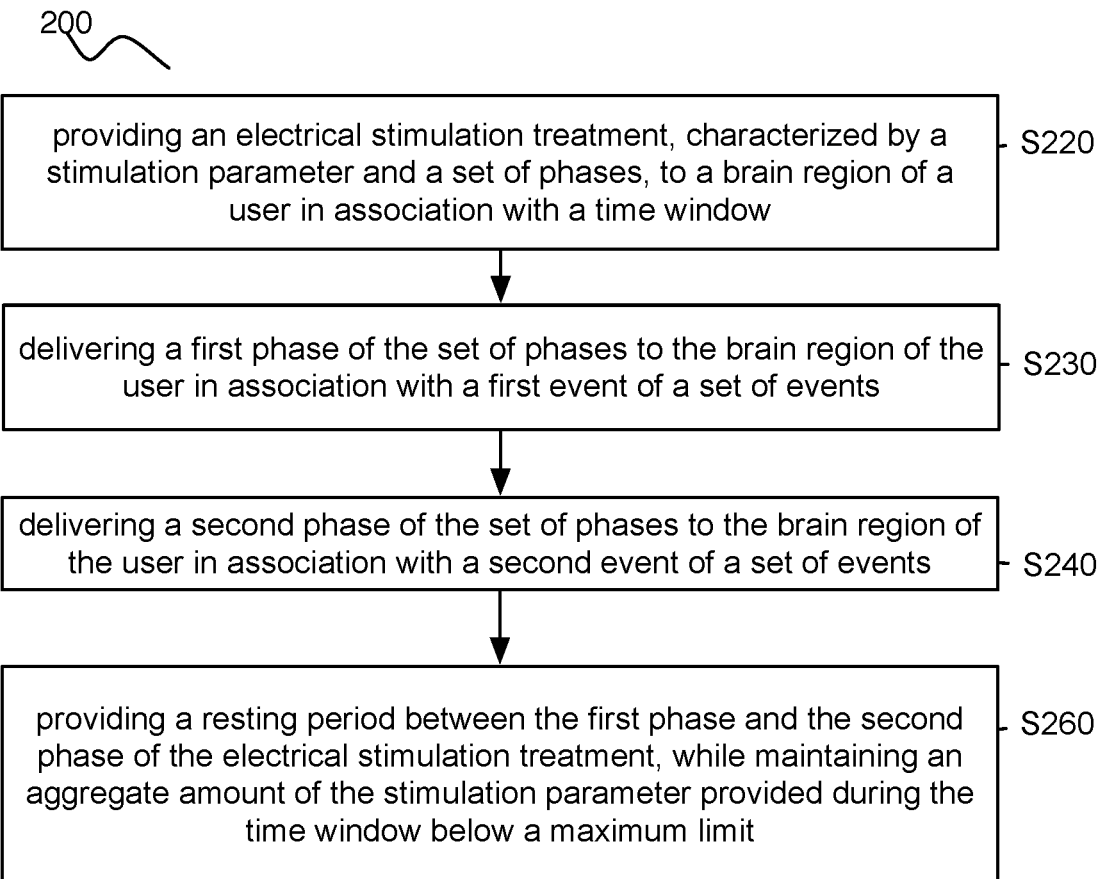
FIG. 3A depicts a schematic of an embodiment of a method for providing electrical stimulation to a user.

In one embodiment, as shown in FIG. 3A, a method 200 for providing electrical stimulation to a user, as the user undergoes a set of events pertaining to neurological activity of the user within a time window, comprises: providing an electrical stimulation treatment, characterized by a stimulation parameter and a set of portions, to a brain region of the user in association with the time window S220, wherein providing the electrical stimulation treatment includes: delivering a first portion of the set of portions of the electrical stimulation treatment to the brain region of the user in association with a first event of the set of events S230; delivering a second portion of the set of portions of the electrical stimulation treatment to the brain region of the user in association with a second event of the set of events S240; and providing at least one resting period between the first portion and the second portion of the electrical stimulation treatment, while maintaining an aggregate amount of the stimulation parameter of the electrical stimulation treatment provided to the user during the time window below a maximum limit S260.

The method 200 functions to strategically provide intermittent electrical stimulation to at least one brain region of the user, wherein intermittency is provided relative to one or more events undergone by the user (e.g., tasks performed by the user, neurological states experienced by the user). Similar to the method 100 described above, the method 200 can additionally function to strategically control provision of an electrical stimulation treatment delivered to a user as the user undergoes a set of events pertaining to neurological activity of the user, wherein the electrical stimulation treatment is provided within specified treatment limits (e.g., for safety, in consideration of maximizing efficacy of the electrical stimulation treatment, etc.). However, the method 100 can additionally or alternatively function to increase an effect of an electrical stimulation treatment provided to the user by modulating the treatment according to an event undergone by the user, without a maximum limit constraint. The method 100 can further optimize provision of a limited amount of electrical stimulation to the user, such that the user only receives electrical stimulation when an actual or anticipated neurological state of the user could be improved by receipt of electrical stimulation.

Similar to the user in Section 1 above, the user can be one or more of: a user diagnosed with a neurological pathology, a user with a neurological condition that can be improved or treated by electrical stimulation, a user would otherwise benefit from enhancement in creativity, attention, focus, cognitive ability (e.g., mathematical ability), learning (e.g., language learning, speech learning), and/or memory (e.g., working memory, declarative memory), and any other suitable user (e.g., human user, non-human user). The set of events can include a set of tasks (or a stage of activity of a task) provided to the user, as described in Section 1 above; however, in some variations of the method 200, the set of events can additionally or alternatively include one or more neurological states of the user characterized by identified neurological signatures, as described in Section 1 above.

Block S220 recites: providing an electrical stimulation treatment, characterized by a stimulation parameter and a set of portions, to a brain region of the user in association with the time window, which functions to improve a neurological state of the user in association with at least one event of the set of events undergone by the user. The electrical stimulation treatment is preferably provided at an electrical stimulation module comprising a head-mounted electrode system configured to provide a TES treatment, as noted above in Section 1 and described in further detail in Section 2 below; however, the electrical stimulation treatment can additionally or alternatively be provided using any other suitable system. Similarly, the stimulation parameter and the set of portions of the stimulation treatment of Block S220 can be analogous to those of Block S120 described above, or can alternatively comprise any other suitable stimulation parameter(s) and/or set of portions.

Block S230 recites: delivering a first portion of the set of portions of the electrical stimulation treatment to the brain region of the user in association with a first event of the set of events, which functions to have a positive effect on the user's cognitive functions (e.g., neural plasticity, neurological state, etc.) relative to the first event of the set of events. The first portion of the set of portions of the electrical stimulation treatment is preferably provided in a manner that avoids or prevents interference from metaplastic mechanisms of the user's brain, which can cause a rebound effect after plasticity is elevated by the electrical stimulation treatment. As such, in some variations the first portion of the set of portions of the electrical stimulation treatment can be provided in a manner that is limited in protraction and/or strength, to facilitate maintenance of or increases in neural plasticity for the user. However, some alternative variations of Block S230 can include provision of one or more portions of the electrical stimulation treatment in a manner that does not avoid interference from metaplastic mechanisms, especially in variations wherein a period of rebounding by the brain can be beneficial to the user.

The first portion of the electrical stimulation treatment is preferably provided with a constant set of stimulation parameters, and as such, can be characterized by constancy in one or more of: a form (e.g., direct current, direct current with a superimposed non-direct current factor, alternating current with one or more frequency components, band-limited, time-varying, etc.), a current amplitude, a stimulation duration, a duty cycle, a stimulation localization/current path of the electrical stimulation treatment, a waveform of the stimulation (e.g., direct current alone, random noise stimulation, variable frequency stimulation, etc.), an on/off status of the stimulation, a polarity of the stimulation (e.g., anodal, cathodal), and any other suitable stimulation parameter. The first portion of the electrical stimulation treatment can alternatively have any suitable uniform or random pattern of one or more of: a current amplitude, a voltage amplitude, a stimulation duration, a duty cycle, a stimulation localization/current path of the electrical stimulation treatment, a waveform of the stimulation (e.g., direct current alone, random noise stimulation, variable frequency stimulation, etc.), an on/off status of the stimulation, a polarity of the stimulation (e.g., anodal, cathodal), and any other suitable stimulation parameter. In examples, the first portion of the electrical stimulation treatment can include a duration between 500 ms to 15 minutes, a positive (e.g., cathodal) polarity, a negative (e.g., anodal) polarity, a current amplitude between approximately 0.5 mA and 2 mA, and a pulsed waveform. Variations of the examples, however, can alternatively be characterized by any other suitable parameter(s).

In relation to avoiding metaplastic mechanisms, the first portion of the electrical stimulation treatment is preferably provided substantially during occurrence of the first event (e.g., a training activity, a task of a set of provided tasks, a detected neurological state, etc.), but can alternatively be provided prior to and/or after occurrence of the first event. For instance, and in relation to Block S240 described below, a portion of the stimulation treatment can be interleaved at a "resting period" between multiple events, such that effects of the stimulation treatment can effect preceding and subsequent events of the set of events. In variations, occurrence of the first event can be detected or observed based upon any one or more of: knowledge of a regimen for providing a set of tasks (e.g., as known by a task administrator, as known based upon a regimen of tasks provided at an application executing on an electronic device, as known based upon a log of usage of an application that facilitates task provision, etc.), detection of task performance based upon raw performance (e.g., based upon user inputs detected at an electronic device that facilitates detection of task performance), detection of task performance based upon detection of biosignals from the user, identification of a neurological signature from a biosignals detection module, and in any other suitable manner.

Block S240 recites: delivering a second portion of the set of portions of the electrical stimulation treatment to the brain region of the user in association with a second event of the set of events S240. Similar to Block S230, Block S240 functions to have a positive effect on the user's cognitive functions (e.g., neural plasticity, neurological state, etc.) relative to the second event of the set of events. Also similar to Block S230, the second portion of the set of portions of the electrical stimulation treatment is preferably provided in a manner that avoids or prevents interference from metaplastic mechanisms of the user's brain, which can cause a rebound effect after plasticity is elevated by the electrical stimulation treatment. As such, in some variations the second portion of the set of portions of the electrical stimulation treatment can be provided in a manner that is limited in protraction and/or strength, to facilitate maintenance of or increases in neural plasticity for the user. However, some alternative variations of Block S240 can include provision of one or more portions of the electrical stimulation treatment in a manner that does not avoid interference from metaplastic mechanisms, especially in variations wherein a period of rebounding by the brain can be beneficial to the user.

Similar to Block S230, the second portion of the electrical stimulation treatment is preferably provided with a constant set of stimulation parameters, and as such, can be characterized by constancy in one or more of: a form (e.g., direct current, direct current with a superimposed non-direct current factor, alternating current with one or more frequency components, band-limited, time-varying, etc.), a current amplitude, a stimulation duration, a duty cycle, a stimulation localization/current path of the electrical stimulation treatment, a waveform of the stimulation (e.g., direct current alone, random noise stimulation, variable frequency stimulation, etc.), an on/off status of the stimulation, a polarity of the stimulation (e.g., anodal, cathodal), and any other suitable stimulation parameter. The second portion of the electrical stimulation treatment can alternatively have any suitable uniform or random pattern of one or more of: a current amplitude, a voltage amplitude, a stimulation duration, a duty cycle, a stimulation localization/current path of the electrical stimulation treatment, a waveform of the stimulation (e.g., direct current alone, random noise stimulation, variable frequency stimulation, etc.), an on/off status of the stimulation, a polarity of the stimulation (e.g., anodal, cathodal), and any other suitable stimulation parameter.

Preferably, the second portion and the first portion of the electrical stimulation treatment are substantially identical to each other in stimulation parameter(s); however, the first and the second portion of the electrical stimulation treatment provided in Blocks S230 and S240 can alternatively be non-identical to each other. In examples, the second portion of the electrical stimulation treatment can include a duration between 500 ms to 15 minutes, a positive (e.g., cathodal) polarity, a negative (e.g., anodal) polarity, a current amplitude of between −2.5 and 2.5 mA, and a pulsed waveform. Variations of the examples, however, can alternatively be characterized by any other suitable parameter(s).

In relation to avoiding metaplastic mechanisms, and similar to Block S230, the second portion of the electrical stimulation treatment is preferably provided substantially during occurrence of the second event (e.g., a training activity, a task of a set of provided tasks, a detected neurological state, etc.), but can alternatively be provided prior to and/or after occurrence of the second event. In variations, occurrence of the second event can be detected or observed based upon any one or more of: knowledge of a regimen for providing a set of tasks (e.g., as known by a task administrator, as known based upon a regimen of tasks provided at an application executing on an electronic device, as known based upon a log of usage of an application that facilitates task provision, etc.), detection of task performance based upon raw performance (e.g., based upon user inputs detected at an electronic device that facilitates detection of task performance), detection of task performance based upon detection of biosignals from the user, identification of a neurological signature from a biosignals detection module, and in any other suitable manner.

Block S260 recites providing at least one resting period between the first portion and the second portion of the electrical stimulation treatment, while maintaining an aggregate amount of the stimulation parameter of the electrical stimulation treatment provided to the user during the time window below a maximum limit. Similar to Block S160 described above, Block S260 functions to increase an effect of the electrical stimulation treatment provided by targeting neurological states associated with events of the user, wherein the user would receive greater benefit from stimulation or modulation of stimulation. Block S260 can additionally function to decrease habituation of the user's brain to the electrical stimulation treatment, by delivering stimulation that has a temporally varying component, as provided by the set of portions (e.g., active periods, non-active periods) of the electrical stimulation treatment.

In Block S260, the resting period is preferably provided between events of the set of events, such that events (e.g., periods of training activity, provision of tasks, etc.) of the set of events substantially coincide with the portions of the electrical stimulation treatment. However, the resting period can alternatively overlap with occurrence of one or more events of the set of events, such that a duration of an event spans a portion of a resting period, and at least a portion of a portion of the electrical stimulation treatment. In Block S260, the resting period can be of equal duration to a duration of a portion of the electrical stimulation treatment, or can alternatively be shorter or longer than a duration of the portion of the electrical stimulation treatment. In examples, the resting period can have a duration from 500 ms to 24 hours; however, variations of the resting period of the examples can alternatively have any other suitable duration.

As noted above, it may be desirable that an aggregated amount of at least one stimulation parameter of the electrical stimulation treatment (e.g., TES) provided during a time window associated with the portions of the electrical stimulation treatment and/or the set of events does not exceed a maximum limit, for example, for safety reasons. As such, a maximum limit for an aggregated value of a stimulation parameter as related to Block S260 can be any one or more of: a maximum dosage (e.g., duration of stimulation, aggregated charge, aggregated charge density, etc.) per day, a maximum dosage per shorter unit of time (e.g., minutes, hours), and any other suitable maximum dosage. In one example, a daily dosage of 30 minutes is an acceptable dosage of tDCS, with higher doses increasing chances of skin irritation for the user and/or other side effects. Furthermore, a remaining allowable stimulation can be tracked in relation to the maximum limit as an accumulated amount of stimulation subtracted from a maximum dosage of stimulation. Here, the accumulated dosage can be increased by an additional portion of the electrical stimulation treatment, and decreased (e.g., according to a logarithmic decay) during a resting period provided in Block S260. Thus, maximizing an effect of electrical stimulation treatment given a maximum acceptable limit of treatment can significantly benefit a user. In variations wherein the electrical stimulation treatment includes TES, the maximum limit is preferably a maximum amount of charge or charge density (e.g., determined based upon current amplitude, duration, duty cycle, and electrode path) that can be delivered to the user per unit time (e.g., the time window). Again, in some variations, the method 100 can substantially omit modulating the electrical stimulation treatment according to a maximum limit constraint, such that modulation is based solely upon a stage of a task and/or a neurological state of the user, without a maximum limit constraint.

Furthermore, in some alternatives to Block S260, a resting period between the first portion and the second portion of the electrical stimulation treatment may not be provided, and instead, modulation between the first portion and the second portion of the electrical stimulation treatment can be performed in any other suitable manner (e.g., with an adjustment in current amplitude, with an adjustment in polarity, etc.).

In a first specific example of the method 200, a first portion and a second portion of stimulation are provided, as in Blocks S230 and S240, each having a duration of 1 minute, and separated by a resting period having a duration of 1.5 minutes. In the first specific example, the first and the second portion of stimulation substantially coincide with a first task and a second task, respectively, each having a duration of approximately one minute. In a variation of the first specific example, a first portion and a second portion of stimulation are provided (e.g., each having a duration between one and 60 seconds), wherein the first portion and the second portion are each coincident with an onset of a respective task or alternatively provided with some offset relative to the onset of the respective task. In the first specific examples, timing between provision of the first and the second portions of the electrical stimulation treatment and the first and the second task can be governed based upon occurrence of the first and the second task. For instance, an electronic device facilitating task provision can signal an electrical stimulation module to provide the portion(s) of the electrical stimulation treatment. Additionally or alternatively, timing between provision of the first and the second portions of the electrical stimulation treatment and the first and the second task can be governed based upon delivery of the first and/or the second portion(s) of the electrical stimulation treatment. For instance, an electrical stimulation module providing the portion(s) of the electrical stimulation treatment can signal a task provision module to provide the task(s) with a suitable relationship to the portion(s) of the electrical stimulation treatment.

In a second specific example of the method 200, an event of the set of events is detected based upon identification of a physiological marker of movement, as detected from a biosignal detection module. In the second specific example, the event can be detected based upon observation of a desynchronization in the alpha band (i.e., a frequency band of neural oscillations) of the user during performance of a task, as measured with a biosignal detection module comprising an EEG electrode or array of electrodes situation proximal to a stimulating electrode configured to transmit portions of the electrical stimulation treatment. As such, periodic movement (e.g., finger movements) associated with the task, can be guided and/or assessed with the biosignals detection module, allowing event-related desynchronization to be measured over multiple events (e.g., similar events). In the second specific example, a current amplitude and/or a duration of a portion of the electrical stimulation treatment can be dynamically modulated, as in Block S260", until event-related desynchronization is maximized.

Figure 3B:
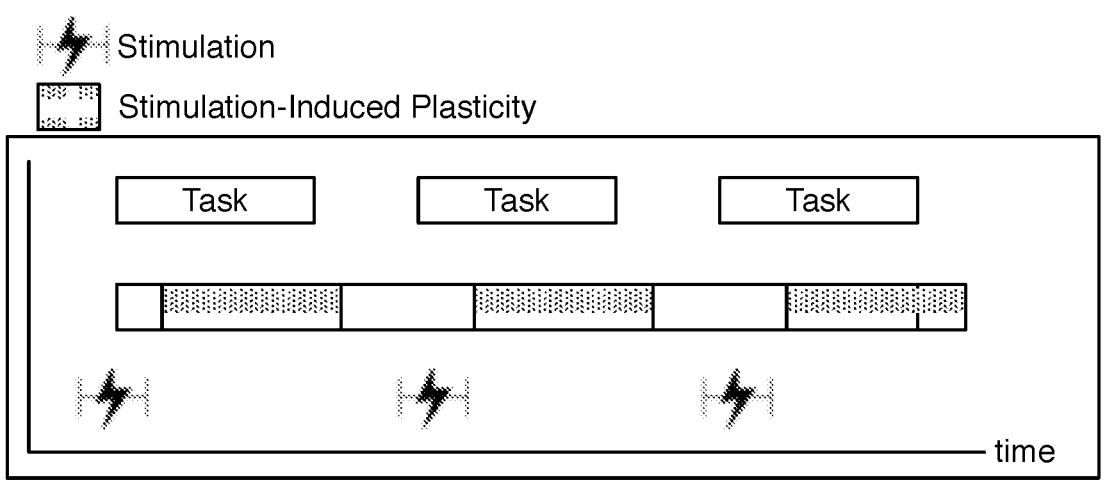
FIG. 3B depicts an example of providing portions of stimulation in relation to a set of provided tasks, in an embodiment of a method for providing electrical stimulation to a user.

In a third specific example of the method 200, a first portion and a second portion of stimulation are provided, as in Blocks S230 and S240, each having a duration of 10 minutes, and separated by a resting period having a duration of 20 minutes. In the first specific example, the first and the second portion of stimulation are provided 5 minutes prior to provision of a physical therapy (PT)/occupational therapy (OT) task having a duration of 20 minutes, followed by a resting period of 10 minutes. As such, each PT/OT task of the third specific example overlaps with a portion of stimulation and a resting period, which can allow a portion of stimulation to have an effect on the user during performance of both a preceding OT/PT task and a subsequent OT/PT task. In the third example, a session of 10-minute stimulation followed by a 20-minute resting period is repeated 3 times, as shown in FIG. 3B, in relation to the provided OT/PT tasks. In the third specific example, the set of tasks provided comprises: 1) a first task that prompts finger-stroking motion for a stroke-affected user, wherein a tablet device is configured to facilitate provision of the task, detection of performance of the task (e.g., at a touch screen), and provision of feedback upon successful performance of the task (e.g., by audible feedback, by visual feedback, by haptic feedback); 2) a second task that prompts finger-tapping motion for a stroke-affected user, wherein a tablet device is configured to facilitate provision of the task, detection of performance of the task (e.g. with an accelerometer), and provision of feedback upon successful performance of the task (e.g., by audible feedback, by visual feedback, by haptic feedback); and 3) a third task that prompts physical object movement for a stroke-affected user, wherein a tablet device is configured to facilitate provision of the task, detection of performance of the task (e.g., at an image sensor), and provision of feedback upon successful performance of the task (e.g., by audible feedback, by visual feedback, by haptic feedback). Variations of the third specific example can, however, include any other suitable pattern of portions of stimulation and resting periods (e.g., 10 minutes of stimulation followed by 25 minutes of rest), any other suitable number of repetitions of sessions, and any other suitable tasks.

In a fourth specific example of the method 200, a first portion and a second portion of cathodal stimulation are provided, as in Blocks S230 and S240, each having a duration of 9 minutes, and separated by a resting period having a duration of one of: 0 minutes, 3 minutes, 20 minutes, 3 hours, and 24 hours. In a variation of the fourth specific example, a first portion and a second portion of anodal stimulation are provided, as in Blocks S230 and S240, each having a duration of 5 minutes, and separated by a resting period having a duration of one of: 0 minutes, 3 minutes, and 30 minutes. In another variation of the fourth specific example, a first portion and a second portion of anodal stimulation are provided, as in Blocks S230 and S240, each having a duration of 13 minutes, and separated by a resting period having a duration of one of: 0 minutes, 3 minutes, 20 minutes, 3 hours, and 24 hours. In another variation of the fourth specific example, a first portion and a second portion of anodal stimulation are provided, as in Blocks S230 and S240, each having a duration of 500 ms, and separated by a resting period having a duration of one of 50 ms and 650 ms. In another variation of the fourth specific example, a first portion and a second portion of anodal stimulation are provided, as in Blocks S230 and S240, each having a duration of 10 minutes, and separated by a resting period having a duration of one of 5 minutes and 25 minutes. In still another variation of the fourth specific example, a first portion and a second portion of anodal stimulation are provided, as in Blocks S230 and S240, each having a duration of 12.5 minutes, and separated by a resting period having a duration of 20 minutes. In still another variation of the fourth specific example, 1-minute-long periods of stimulation can be provided to a user, wherein the 1-minute-long periods are separated by 1.5 minute-long resting periods, for a desired duration of time (e.g., over the course of 1 hour). In any of the variations of the fourth specific examples, the first and/or the second portion of stimulation can be provided prior to, during, and/or after a respective task, and responses to the portions of stimulation can be detected by way of evoked potentials of the user.

Variations of the specific examples described above can include any suitable repetition of providing the portion(s) and the resting periods of the electrical stimulation treatment.

Another embodiment of the methods 100, 200, wherein stimulation is targeted to detected neurological states, is described further in Section 1.2 below:

1.2 Method—Stimulation Targeted to Detected Neurological States

Figure 4:
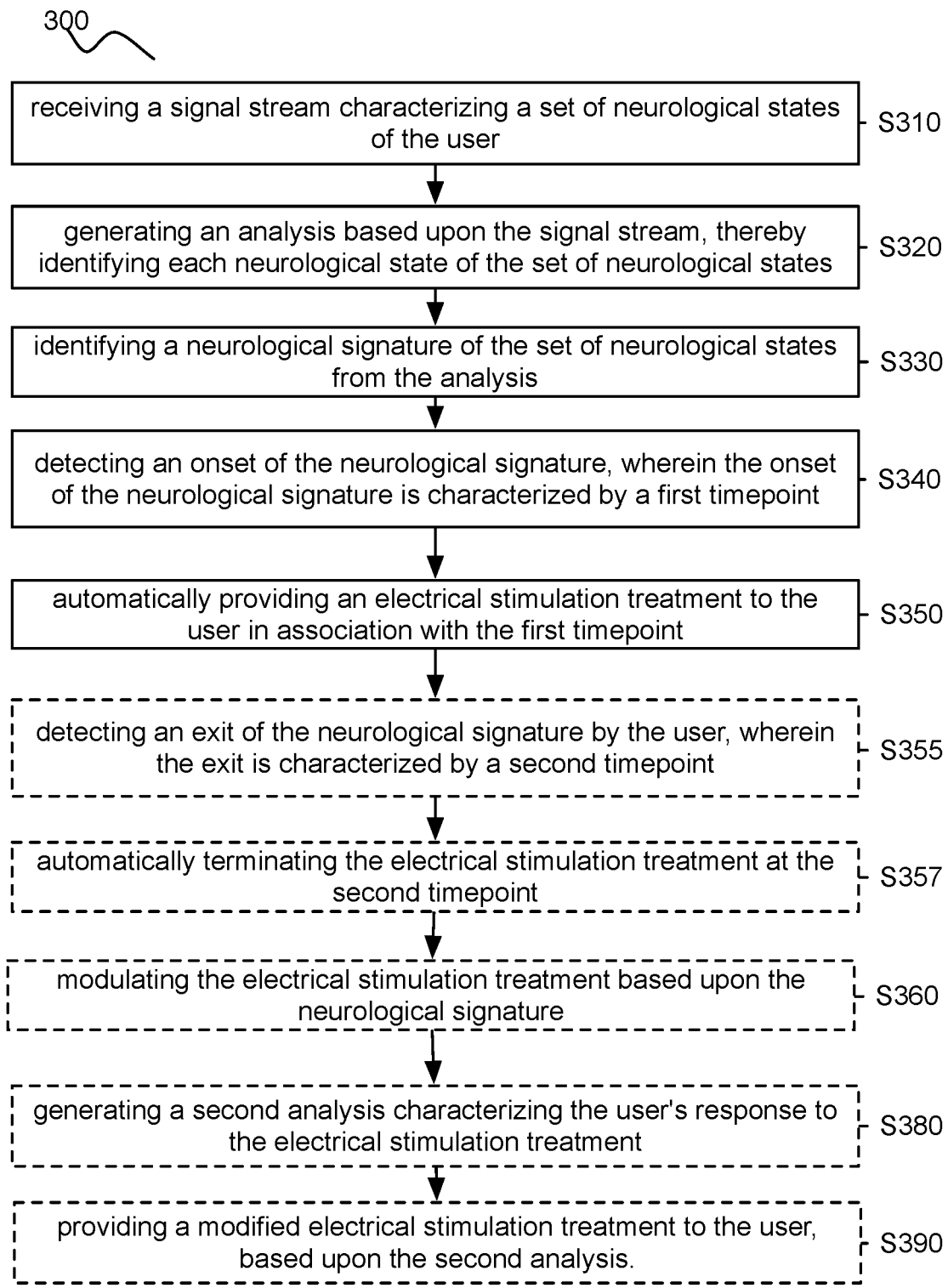
FIG. 4 depicts a schematic of an embodiment of a method for providing electrical stimulation to a user.

In one embodiment, as shown in FIG. 4, a method 300 for providing electrical stimulation to a user comprises: at a biosignal detection module, receiving a signal stream characterizing a set of neurological states of the user S310; at a processing system, generating an analysis based upon the signal stream, thereby identifying each neurological state of the set of neurological states characterized by the signal stream S320; identifying a neurological signature of the set of neurological states from the analysis S330; detecting an entry of the neurological state signature, wherein the entry of the neurological signature is characterized by a first time point S340; and at an electrical stimulation module, automatically providing an electrical stimulation treatment to the user in association with the first timepoint S350.

The method 300 can further comprise detecting an exit of the neurological signature by the user, wherein the exit of the neurological signature is characterized by a second timepoint S355; automatically terminating the electrical stimulation treatment at the second timepoint S357; modulating the electrical stimulation treatment provided to the user based upon the neurological signature S360, wherein modulating comprises delivering a portion of the set of portions of the electrical stimulation treatment to the brain region of the user, while maintaining an aggregate amount of a stimulation parameter of the electrical stimulation treatment provided to the user during the time window below a maximum limit; generating a second analysis characterizing the user's response to the electrical stimulation treatment S380; and providing a modified electrical stimulation treatment to the user, based upon the second analysis S390.

The method 300 functions to automatically transmit electrical stimulation to a user in association with detected neurological signatures, as observed using a biosignal detection module. The method 300 can be used to enhance motor learning or any other suitable type of learning, and can additionally or alternatively be used to facilitate consolidation of learning by a user. The method 300 can also be used to enhance or modulate working memory and declarative memory. In some variations, the electrical stimulation treatment, matched with a specific user neurological state, can induce a physiological response that benefits the user. In examples, the method 300 can thus be used to enhance learning and/or memory retention during a specific neurological state (e.g., sleep states, phases of a sleep cycle, wake states), by automatically providing an electrical stimulation treatment to the user as the user is experiencing the specific neurological state. In other examples, a user's response to an electrical stimulation treatment, provided by the method 300, can be indicative of a neurological condition of the user, such that the method 300 can be used to identify a unique neurological condition of the user in order to provide a diagnosis for the user, and/or to personalize electrical stimulation treatment for the user, based upon the identification of the neurological condition. In other examples, the method 300 can be used in any other suitable manner to identify neurological states and/or neurological conditions of a user, and to provide electrical stimulation treatments upon identification or detection of user specific neurological states.

In some variations, the user can be a patient diagnosed with a neurological condition (e.g., learning impairment, memory-affecting condition, cognitive impairment), such that the method 300 is used to facilitate management of the user's neurological condition by reversing damage resulting from the neurological condition, halting damage resulting from the neurological condition, and/or by enabling the user to cope with the neurological condition. In additional variations, the user can be undiagnosed with a neurological condition, and the method 300 can be used as a tool to enhance, consolidate, and/or positively affect the user's learning behavior in any suitable manner. In still other variations, the user can be undiagnosed with a neurological condition, and the method 300 can be used to enhance the user's memory retention and/or facilitate consolidation of the user's memories. As such, the user can be a patient with a neurological condition, or can alternatively be a user without a neurological condition.

Block S310 recites: receiving a signal stream characterizing a set of neurological states of the user, and functions to provide biosignal data that can be processed and analyzed to determine one or more neurological state signatures of the user. Similar to Block S130 above, Block S310 is preferably performed at a biosignal detection module, such as an embodiment of the biosignal detection module described in Section 2 below; however, Block S310 can alternatively be performed using any other suitable system comprising a biosignal sensor system. Similar to Block S130 above, the signal stream received in Block S310 can comprise one or more of: bioelectrical signals from a brain region of the user, any other suitable biolelectrical signals, biosignals, environmental signals, and any other suitable signals from the user or the user's environment. In some variations, set of signals received in Block S310 can thus provide a comprehensive characterization of the user's cognitive, physiological, and/or environmental state based upon multiple sensor types, in order to provide a basis for user state-matched electrical stimulation. In other variations, the set of signals received in Block S310 can provide a simpler characterization of the user's cognitive state, based solely upon a single signal type (e.g., EEG signals) received at a biosignal detection module. Also similar to Block S130 above, the signal stream of Block S310 can include signals from multiple sensor channels, a single sensor channel, and/or multiplexed signals from one region of the user. Additionally or alternatively, the signal stream can also be a compressed, filtered, conditioned, amplified, or otherwise processed version of raw signals from one or more sensors.

Preferably, the signal stream is received continuously in Block S310; however, the signal stream can additionally or alternatively be received intermittently and/or when prompted by the user or other entity. Additionally, the signal stream is preferably received in real time, in order to facilitate real time or near-real time analysis in Block S320, and/or real time or near-real time stimulation provision in Block S350. However, the signal stream can alternatively be received with any suitable temporal delay, or in any other suitable manner. For example, in variations wherein the user's neurological states undergo a cyclic pattern, the set of signals can be received with a temporal delay that is synchronized with the cyclic pattern, such that a set of signals characterizing one cycle is received in synchronization with another cycle being experienced by the user.

In Block S310, the set of signals preferably characterizes a set of neurological states, indicative of cognitive states of the user. In one variation, the set of neurological states can comprise states or phases of a sleep cycle, including rapid eye movement (REM) sleep states and non-rapid eye movement (NREM) sleep states. In this variation, NREM sleep states can further comprise NREM stage 1 sleep, NREM stage 2 sleep, and NREM stage 3 sleep. REM sleep is characterized in signals by rapid low-voltage EEG signals defined by high frequency saw-tooth waves, along with ocular motion, which can be detected and received using an EEG sensor, an EMG sensor, and/or an EOG sensor of the biosignal detection module. NREM stage 1 sleep is characterized in signals by a transition from alpha wave neural oscillations to theta wave neural oscillations (e.g., with a frequency of 4-7 Hz), along with muscle twitching (e.g., myoclonus), and/or hallucinations, which can be detected and received using an EEG sensor, an EMG sensor, and/or an MEG sensor. NREM stage 2 sleep is characterized in signals by sleep spindles ranging from 11-16 Hz and K-complexes, along with a decrease in muscular activity, which can be detected and received using an EEG sensor, an EMG sensor, and/or an MEG sensor. NREM stage 3 sleep (i.e., slow-wave sleep) is characterized in signals by a minimum of 20% delta waves ranging from 0.5-2 Hz and a peak-to-peak amplitude greater than 75 microvolts, which can be detected and received using an EEG sensor. NREM stage 3 sleep is physiologically characterized by neurons in multiple brain regions (e.g., hippocampus, prefrontal cortex, and visual cortex) firing in a pattern that is similar to, but accelerated in comparison to a pattern in which the neurons fired during learning of a day's events. User's typically experience four to five REM-NREM sleep cycles per night, with cycle lengths decreasing progressively through the night, and a shift from increased NREM stage 3 sleep earlier in the night to increased REM sleep later in the night. In this variation, the method 100 can then be configured to provide stimulation matched with a given sleep state.

In another variation, the set of neurological states can comprise states or phases experienced by a user during quiet wakefulness, sleep, and/or anesthetic states, wherein brain signals exhibit slow (e.g., less than 1 Hz), large amplitude oscillations in electrical potentials. The oscillations result from synchronization in the activity of large numbers of neurons in the cortex, and comprise down states (e.g., troughs) characterized by low voltages produced by synchronized neurons in a hyperpolarized state, and up states (e.g., peaks), characterized by high voltages produced by synchronized neurons in a depolarized state. The set of neurological states can thus comprise down states and up states, and/or any other relevant neurological state(s) experienced by the user during quiet wakefulness, sleep, and/or anesthetic states. In this variation, the method 100 can then be configured to provide stimulation matched with a given state of a large amplitude oscillation.

In yet another variation, the set of neurological states can comprise neurological states experienced by a user during a state of stress and/or a state of heightened alertness, such that the method 100 can be configured to provide targeted stimulation during stress states and/or alert states, as detected by a biosignal detection module. In yet another variation, the set of neurological states can comprise neurological states indicative of a learning state of the user in association with performance of a set of tasks. The set of neurological states can, however, comprise any other suitable neurological state of the user.

Block S320 recites: generating an analysis based upon the signal stream, thereby identifying each neurological state of the set of neurological states characterized by the signal stream, and functions to transform the set of signals into an analysis that identifies aspects of each neurological state experienced by the user during reception of the set of signals. Block S120 is preferably performed at a processing subsystem, wherein the processing subsystem can be integrated with a biosignal detection module, or can be remote from the biosignal detection module. The processor is preferably an embodiment of the processing subsystem described in Section 2 below, but can be any other suitable processing subsystem configured to facilitate identification of each neurological state characterized by the signal stream received in Block S310. In some variations, the processing subsystem can implement a machine learning algorithm that automatically recognizes specific neurological states (e.g., sleep states, alert states, states of a large amplitude oscillation) based upon the analysis of the received set of signals, as described in relation to Block S140 above. Block S320 can, however, be implemented at a processing subsystem configured to implement any other suitable algorithm.

For each neurological state captured in the signal stream, the analysis can characterize a neurological state initiation event (e.g., signal characteristic and timepoint), neurological state termination event (e.g., signal characteristic and timepoint), neurological state duration, cyclic behavior of multiple sequential neurological states, and/or any other suitable aspect of a neurological state. Furthermore, the analysis can characterize regular and/or non regular variations in neurological state cycles. In one such example, the analysis can characterize the regular progression in sleep cycle behavior for a user, including a per-cycle decrease in NREM sleep state duration, a per-cycle increase in REM sleep state duration, and/or a net decrease in cycle-to-cycle duration. Each neurological state can be automatically identified based upon known neurological state signal characteristics (e.g., amplitude, frequency, waveform, sequence between other neurological states, etc.), and/or can be manually identified by a user or other entity at a user interface. Preferably, each neurological state identified in the analysis is tagged with an identifier linked with aspects of the neurological state and furthermore, subsequent occurrences of the neurological state, captured in subsequent occurrences of signal detection and reception, are preferably similarly tagged with the identifier. However, each neurological state can be identified in any other suitable manner, and an identification of a neurological state can be used to identify reoccurrences of the neurological state in any other suitable manner.

In one variation, the analysis can characterize states of a sleep cycle of a user, thus providing a personalized analysis of the sleep state characteristics for the user. In another variation, the analysis can characterize states of a large amplitude oscillation (e.g., experienced during quiet wakefulness, experienced during slow wave sleep, experienced in an anesthetic condition). In yet another variation, the analysis can characterize cognitive states of an alert or stressed user. The analysis can, however, identify and characterize any other suitable neurological state of the user in order to facilitate neurological state-matched electrical stimulation.

Block S330 recites: identifying a neurological signature of the set of neurological states from the analysis, and functions to select at least one neurological state of the user, from the analysis, intended to be matched with an electrical stimulation treatment. Similar to Block S320, Block S330 can be performed at a processing subsystem, such as an embodiment of the processing subsystem described in Section 2 below. Furthermore, identification of a neurological signature can be performed manually by a user at a user interface, and/or can be performed automatically at the processing subsystem. Furthermore, multiple neurological states can be selected as neurological signatures, such that the method 300 can provide electrical stimulation matched to multiple neurological state signatures of the user. In one variation, a portion of a neurological state can be a selected target for electrical stimulation, and in another variation, a transition between neurological states can be a selected target for electrical stimulation. In yet another variation, a combination of targets can be selected as a trigger for electrical stimulation (e.g., a transition between neurological states, followed by a neurological state event can be a selected target). Other variations of Block S330 can, however, can comprise identification of any suitable neurological state signature, target portion of a neurological state, target transition between neurological states, and/or any characteristic target (or combination of targets) for target-matched electrical stimulation.

In one example of Block S330 for sleep state-matched stimulation, identifying a neurological state signature can comprise a NREM stage 3 (i.e., slow-wave sleep) neurological state, characterized by an entry, an exit, and a duration. Such characteristics of the target NREM stage 3 neurological state can then be used in an example of Block S140, in order to create a trigger that automatically initiates provision and/or termination of an electrical stimulation treatment in examples of Block S150 and/or Block S160.

In another example of Block S330 for stimulation matched with states of a large amplitude oscillation, identifying a neurological state signature can comprise identifying a down state of a large amplitude oscillation, characterized by oscillation trough features (e.g., minimum signal voltage). The down state can further be characterized by an entry and an exit (e.g., inflection points that bound the minimum signal voltage), as well as a duration (e.g., spacing between inflection points that bound the minimum signal voltage). Such characteristics of the target down state can then be used in an example of Block S140, in order to create a trigger that automatically initiates provision and/or termination of an electrical stimulation treatment in examples of Block S350 and/or Block S355.

In another example of Block S330 for stimulation matched with states of a large amplitude oscillation, identifying a neurological state signature can comprise identifying an up state of a large amplitude oscillation, characterized by oscillation peaks (e.g., maximum signal voltage). The up state can further be characterized by an entry and an exit (e.g., inflection points that bound the maximum signal voltage), as well as a duration (e.g., spacing between inflection points that bound the maximum signal voltage). Such characteristics of the target up state can then be used in an example of Block S340, in order to create a trigger that automatically initiates provision and/or termination of an electrical stimulation treatment in examples of Block S350 and/or Block S355.

In some variations, Blocks S310 through S330 can function to calibrate a biosignal detection module-processing subsystem unit, such as the one described in Section 2 below, thus preparing the unit to automatically perform neurological state-matched electrical stimulation treatments in Blocks S340 and S350. Furthermore, Blocks S310-S330 can additionally or alternatively be performed in an iterative pattern to collect, identify, and refine identification of neurological state signature(s) for target-matched electrical stimulation.

Block S340 recites: detecting an entry of the neurological signature, wherein the entry of the neurological signature is characterized by a first timepoint. Block S340 functions to create a trigger whenever a characteristic of the neurological state signature (e.g., entry of the neurological state, transition into the neurological state) is detected. Preferably, the characteristic of the neurological state signature is detected at the biosignal detection module of one embodiment of Block S210; however, the characteristic of the neurological state signature can be detected in any other suitable manner. The entry of the neurological state signature is preferably a bioelectrical signal (e.g., EEG signal, EOG signal, EMG signal, MEG signal) event that defines an initiation of the neurological state signature event; however, the entry of the neurological state signature event can additionally or alternatively comprise any other suitable physiological signal event (e.g., respiratory event, galvanic skin impedance event, heart rate event, etc.). The first timepoint is thus an initiation timepoint of a time window spanning the entire neurological state signature event. In a first variation, the first timepoint can define the first occurrence of an EEG signal peak-to-peak amplitude greater than 75 microvolts, characteristic of an entry of a slow-wave sleep state. In a second variation, the first timepoint can define an inflection point prior to a trough of an EEG signal, characterizing an entry of a down state of a large amplitude oscillation. In a third variation, the first timepoint can define an inflection point prior to a peak of an EEG signal, characterizing an entry of an up state of a large amplitude oscillation. In a fourth variation, the first timepoint can define an entry of heightened heart rate coupled with increased neurological activity (e.g., a high frequency and high amplitude EEG signal set), characteristic of an entry of a stress state. Other variations of Block S140 can, however, comprise automatically detecting an entry of any other suitable neurological state signature, using any suitable system.

Block S350 recites: automatically providing an electrical stimulation treatment to the user in association with the first timepoint, and functions to deliver an electrical stimulation treatment temporally matched with a neurological state signature experienced by the user. Block S350 is preferably performed at an electrical stimulation module, such as the electrical stimulation module described in Section 2 below; however, Block S350 can alternatively be performed using any other suitable electrical stimulation module. Similar to the methods 100, 200 described above, the electrical stimulation treatment is preferably transcranial electrical stimulation (TES); however, the stimulation treatment can additionally or alternatively comprise any other form of electrical stimulation configured to stimulate any other suitable region of the user's body, with any suitable penetration depth, and/or any suitable target tissue structure (e.g., neural, musculoskeletal). The electrical stimulation treatment can be similarly characterized by at least one stimulation parameter and a set of phases. Furthermore, the electrical stimulation treatment can comprise multiple forms, wherein the forms can be performed simultaneously and/or in sequence.

The electrical stimulation treatment automatically provided in Block S350 can be uniform (e.g., characterized by a regular pattern or waveform, characterized by a constant intensity, characterized by a constant frequency). However, the electrical stimulation treatment provided can alternatively be non-uniform. Furthermore, in variations, the electrical stimulation treatment can comprise using multiple treatments at different locations, in order to stimulate formation of neural connections in synchronization with a target neurological state (e.g., by Hebb's rule). The multiple treatments in these variations can be identical, can be provided at two or more anodal electrodes positioned at different locations on the user's skull (with cathodal electrodes positioned elsewhere), and can be provided with a delay between treatments (e.g., up to a toms delay). Alternatively the multiple treatments can be non-identical (e.g., comprise different forms of electrical stimulation, can comprise different treatment parameters), can be provided using any suitable electrode configuration, and/or can be provided without any substantial delay between treatments. Modulation of a delay between treatments can modulate the strength of formed neural connections.

In a first example, the electrical stimulation treatment can comprise a tDCS treatment and can be delivered to the user upon detection of an entry of slow-wave sleep (i.e., NREM stage 3) at a first timepoint, which can function to improve declarative memory. The tDCS treatment can target the user's prefrontal cortex (e.g., by way of a electrode system configured to stimulate the prefrontal cortex) during replaying of recent memory sequences in the prefrontal cortex during slow-wave sleep. The tDCS treatment can additionally or alternatively target the user's visual cortex and/or hippocampus, the latter e.g. by stimulating neocortical structures that project to the hippocampus via entorhinal cortex, during replaying of recent memory sequences in the visual cortex and/or hippocampus during slow-wave sleep. In the first example, delivering the tDCS treatment while the user is sleeping can allow the user to be in a non-motile, restful state, can take advantage of compressed replay of neural activity during sleep, and can enhance declarative memory of the user while the user is in a potentially less stressful state. The electrical stimulation treatment in the first example can be delivered in a clinical or research setting, or can alternatively be delivered in a non-clinical setting (e.g., at a portable, wearable system). In a variation of the first example, the electrical stimulation treatment can alternatively be provided upon detection of an entry of REM sleep, which can function to enhance non-declarative memory of the user.

In a second example, the electrical stimulation treatment can comprise a TES treatment and can be delivered to the user upon detection of an entry of an up state of a large amplitude oscillation at a first timepoint, which can function to selectively induce long term potentiation (LTP) of neural synaptic activity in the user. The TES treatment can be provided at the motor cortex of the user (e.g., using a sensor system configured to selectively provide TES to the motor cortex), where inducing LTP can enhance or modulate recent motor learning. The user in the second example can be a stroke patient or other user with a neurological derived impairment of motor function, or can be any other suitable user who desires modulation of motor learning. In a variation of the second example, the electrical stimulation treatment can comprise a TES treatment and can be delivered to the user upon detection of an entry of a down state of a large amplitude oscillation at a first timepoint, which can function to selectively induce long term depression (LTD) of neural synaptic activity. In other variations of the second example, the TES treatment can be provided to the user sequentially upon detection of an entry of an up state and upon detection of an entry of a down state, such that LTP and LTD are cyclically induced in the user.

In a third example, the electrical stimulation treatment can comprise a TES treatment and can be delivered to the user upon detection of an entry of a stressed or alert state, which can function to increase working memory and/or declarative memory in the user. The TES treatment can be an anodal tDCS treatment provided at the prefrontal cortex of the user (e.g., using a sensor system configured to selectively provide tDCS to the prefrontal cortex), where stimulation can enhance or modulate attention, focus, cognitive control, or working memory. The TES treatment can additionally or alternatively be provided at the left dorsolateral prefrontal cortex of the user, where stimulation can enhance or modulate attention, focus, cognitive control, or declarative memory. In variations of the third example, the electrical stimulation treatment can be provided, upon detection of the stress state, at regions of the brain known to modulate stress, such that a stress response of the user can be modulated (e.g., decreased, stabilized, etc.). As such, the third example can increase focus during stress states, or can function to modulate a stress response in the user.

In a fourth example, a first electrical stimulation treatment can be provided at a first region of the user's brain, and a second electrical stimulation treatment can be provided at a second region of the user's brain, upon detection of an entry of a neurological state signature. The first electrical stimulation treatment can comprise a tVFS treatment characterized by a first stimulation waveform, and the second electrical stimulation treatment can be identical to the first electrical stimulation treatment, delivered toms after the first electrical stimulation treatment. In the fourth example, the first region can comprise Broca's area, and the second region can comprise Wernicke's area, such that the method 100 functions to automatically promote growth of neurological connections between Broca's area and Wernicke's area upon detection of a neurological state signature at which stimulation would be most effective. The fourth example can thus provide treatment of Broca's aphasia, by stimulating neural connections between severed brain regions. Variations of the fourth example can comprise stimulating any other suitable combination of multiple brain regions, with or without a delay, in order to promote growth of neural connections upon detection of a neurological state signature.

As shown in FIG. 1, the method 100 can further comprise Block S355, which recites: detecting an exit of the neurological signature by the user, wherein the exit of the neurological state signature is characterized by a second timepoint. Block S160 functions to establish a second trigger that can be used to terminate provision of an electrical stimulation treatment, such that the electrical stimulation treatment is isolated to a given time window characterized a first timepoint and a second timepoint. Similar to Block S140, the exit of the neurological state signature is preferably a bioelectrical signal (e.g., EEG signal, EOG signal, EMG signal, MEG signal) event that defines an end of the neurological state signature event; however, the end of the neurological state signature event can additionally or alternatively comprise any other suitable physiological signal event (e.g., respiratory event, galvanic skin impedance event, heart rate event, etc.). In a first variation, the second timepoint can define the last occurrence of an EEG signal peak-to-peak amplitude greater than 75 microvolts, characteristic of an end of a slow-wave sleep state. In a second variation, the second timepoint can define an inflection point after a trough of an EEG signal, characterizing an exit of a down state of a large amplitude oscillation. In a third variation, the second timepoint can define an inflection point after a peak of an EEG signal, characterizing an exit of an up state of a large amplitude oscillation. In a fourth variation, the second timepoint can define an entry of a reduced heart rate coupled with decreased neurological activity (e.g., a low frequency and high amplitude EEG signal set), characteristic of an exit of a stress state. Other variations of Block S160 can, however, comprise automatically detecting an exit of any other suitable neurological state signature, using any suitable system.

Also shown in FIG. 1, the method 100 can further comprise Block S357, which recites: automatically terminating the electrical stimulation treatment at the second timepoint. Block S170 functions to confine provision of an electrical stimulation treatment to a time window spanning the neurological state signature. As such, Block S170 enables the method 100 to automate initiation and termination of the electrical stimulation treatment(s), in synchronization with a neurological state signature event. In one variation, Block S170 can comprise automatically shutting off a system configured to provide the electrical stimulation treatment. In another variation, Block S170 can comprise automatically displacing electrodes (e.g., by an actuator) configured to deliver the electrical stimulation treatment. Other variations of Block S170 can, however, comprise automatically terminating the electrical stimulation treatment in any other suitable manner.

Similar to the methods 100, 200 described above, the method 300 can further include Block S360, which recites: modulating the electrical stimulation treatment provided to the user based upon the neurological signature S360, wherein modulating comprises delivering a portion of the set of portions of the electrical stimulation treatment to the brain region of the user, while maintaining an aggregate amount of a stimulation parameter of the electrical stimulation treatment provided to the user during the time window below a maximum limit. Modulation in Block S360 can be performed in a manner similar to that of Blocks S160 and S260 described above, or in any other suitable manner.

In one example for improving a desired learning rate in a user, an electrical stimulation treatment (e.g., anodal stimulation of the primary motor cortex of the user) can be provided to the user as in Block S350, during performance of a task (e.g., a training activity for a user under going rehabilitation). Modulation of the electrical stimulation treatment to produce an improved learning rate can be performed according to Block S160, wherein a controller modulates an amount and/or a duration of a portion of the electrical stimulation treatment to produce the improved learning rate of the user. In the example, if a rate of learning (e.g., as assessed by an analysis of performance of the task by the user, as assessed by biosignals detection) is within desired limits, the controller can be configured to deliver stimulation or intermittent stimulation without any adjustment, under an assumption that the electrical stimulation treatment being supplied is effective. However, if the rate of learning is above an upper limit, the controller can be configured to reduce a parameter (e.g., current amplitude, duration) of the electrical stimulation treatment, and if the rate of learning is below a lower limit, the controller can be configured to increase or to decrease (e.g., to facilitate re-normalization of homeostatic mechanisms counteracting neural plasticity) a parameter of the electrical stimulation treatment. In this example, stimulation can be resumed and learning re-assessed (e.g., based upon biosignal detection), after a hiatus (e.g., a one to 20 minute hiatus).

Also shown in FIG. 1, the method 100 can further comprise Block S380, which recites: generating a second analysis characterizing the user's response to the electrical stimulation treatment. Block S380 functions to provide an analysis of a user response to an electrical stimulation treatment, wherein the analysis serves as a basis for providing a modified electrical stimulation treatment to the user in Block S190. The analysis can characterize an effect of the electrical stimulation treatment, for example, by way of metrics quantifying an effect of the treatment (e.g., metrics that quantify user comfort, metrics that quantify effectiveness, metrics that quantify physiological a physiological response). The analysis can additionally or alternatively comprise user-populated data, collected from the user or another entity, by way of a user survey or other means. The second analysis can be provided to the user, and/or can be used to automatically modulate electrical stimulation treatment parameters in variations of the method 100 comprising Block S190.

Also shown in FIG. 1, the method 100 can further comprise Block S190, which recites: providing a modified electrical stimulation treatment to the user, based upon the second analysis. Block S190 functions to automatically modulate an electrical stimulation treatment provided to the user, in response to the second analysis generated in Block S180. As such, the modified electrical stimulation treatment can be characterized by any one or more of: adjusted first and second timepoints (e.g., a different time window) relative to a given neurological state signature, an adjusted stimulation intensity, an adjusted stimulation frequency, an adjusted stimulation waveform, a different form of stimulation, a different configuration of stimulation-providing electrodes, and any other suitable stimulation parameter. Preferably, the adjusted stimulation parameters are automatically adjusted, based upon the second analysis, at a processor coupled to a controller, wherein the controller is configured to control deliverance of treatment parameters. However, the adjusted stimulation parameters can be adjusted and provided in any other suitable manner.

The method 100 can further comprise any other suitable block(s) or step(s) configured to facilitate automatic provision of an electrical stimulation treatment, matched to a neurological state signature of a user, and/or enhance treatment effectiveness using any other suitable manner. For example, the method can further comprise transmitting at least one of the analysis and the second analysis to an entity, generating an aggregate analysis based upon analyses from multiple users, and modulating an electrical stimulation treatment based upon the aggregate analysis. Other examples and variations of the method 100, can however, be configured to facilitate automatic provision of an electrical stimulation treatment, matched to a neurological state signature of a user in any other suitable manner.

As a person skilled in the field of biosignals will recognize from the previous detailed description and from the figures and claims, modifications and changes can be made to the preferred embodiments of the methods 100, 200, 300 without departing from the scope of the methods 100, 200, 300.

2. System

Figure 5:
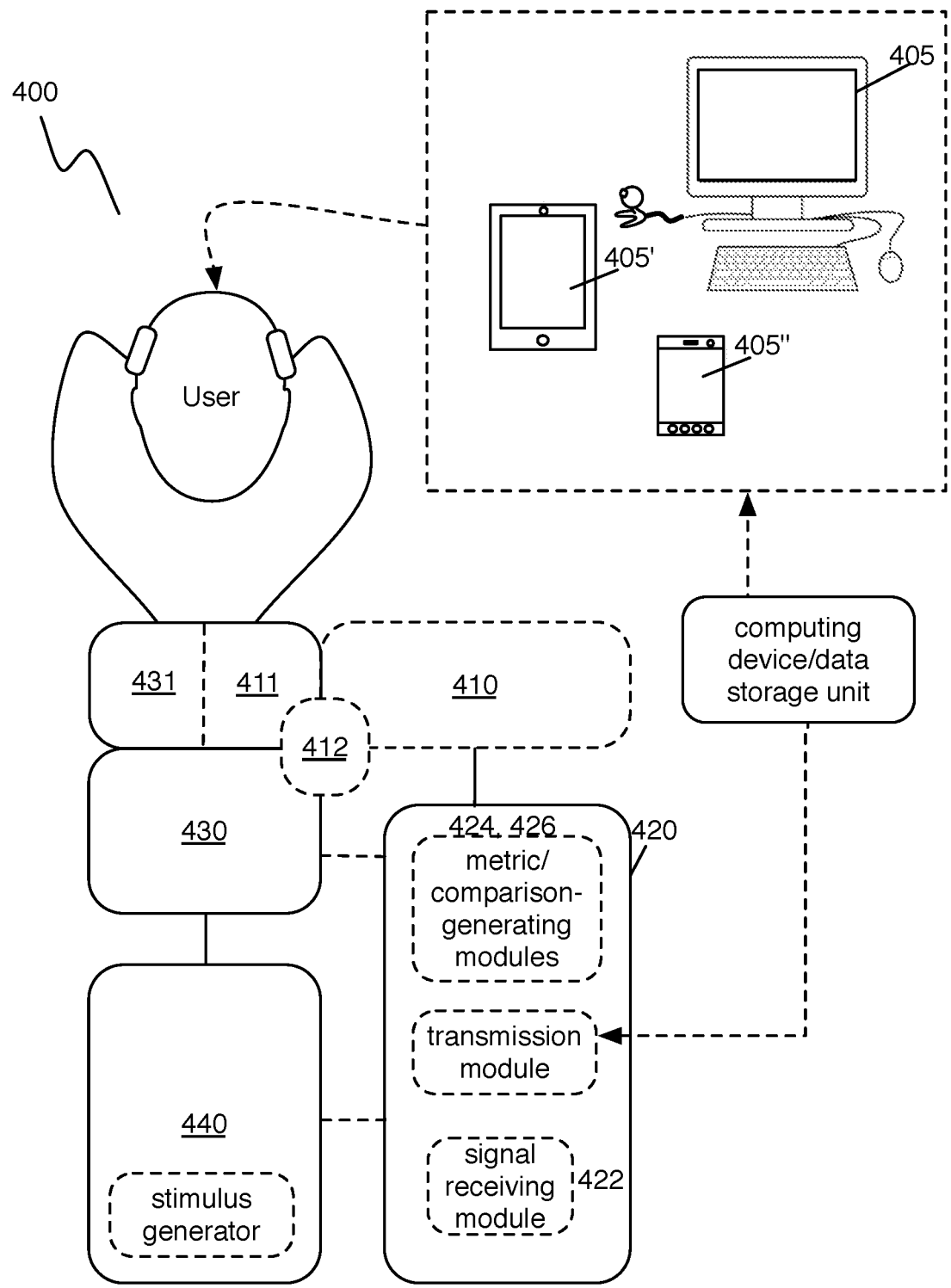
FIG. 5 depicts a schematic of a system for providing electrical stimulation to a user.

As shown in FIG. 5, an embodiment of a system 400 for providing electrical stimulation to a user comprises: a user interface 405 of an application configured to provide a set of tasks to the user; a biosignal detection module 410 configured to enable detection of a signal stream from the user as the user performs each task in the set of tasks; a processing subsystem 420 coupled to the biosignal detection module 410 and comprising a module configured to identify a set of neurological signatures, corresponding to each task of the set of tasks, based upon the signal stream, and a module configured to generate a set of comparisons between a set of neurological metrics derived from the set of neurological signatures and at least one condition; an electrical stimulation module 430 configured to generate and transmit an electrical stimulation treatment to the user in cooperation with provision of the set of tasks; and a controller 440 coupled to the processor and the electrical stimulation module, wherein the controller is configured to control provision and modulation of the electrical stimulation treatment based upon the set of comparisons, and wherein the processing subsystem and the controller are configured to maintain a parameter of the electrical stimulation treatment provided below a maximum limit. In some variations, the system can substantially omit the biosignal detection module 410, such that modulation of the electrical stimulation treatment in is based upon a stage of a task of the set of tasks, or the user's performance of a phase of a task of the set of tasks, without consideration of a neurological state of the user detected by the biosignal detection module 410. Furthermore, in some variations, the method 100 can substantially omit modulating the electrical stimulation treatment, by the processor 420 and the controller 440, according to a maximum limit constraint, such that modulation is based solely upon a phase of a task and/or neurological state of the user, without a maximum limit constraint. The system 400 is preferably configured to perform an embodiment of the methods 100, 200, 300 described in Section 1, 1.1, and 1.2 above, but can additionally or alternatively be configured to perform any other suitable method.

The user interface 405 functions to convey the set of tasks to the user, such that the user can receive and interact with the set of tasks as biosignals are collected from the user. The user interface is preferably implemented at least in part at an application executing on an electronic device (e.g., mobile device, computing device, web browser, etc.) of the user, but can additionally or alternatively be implemented in any other suitable manner. The user interface preferably comprises a display, a camera (e.g., for eye tracking information), an audio unit (e.g., speaker, microphone), and an input module (e.g., keyboard, keypad, voice command module, etc.), and can additionally or alternatively comprise any other suitable features that promote or enable user interaction.

The biosignal detection module 410 functions to detect a signal stream from the user, wherein the signal stream can be processed and analyzed to characterize a neurological state of the user as the user performs a task of the set of tasks. The biosignal detection module 410 is preferably configured to detect bioelectrical signals from the user, but can additionally or alternatively be configured to detect any other suitable physiological and/or environmental signal relevant to the user. The biosignal detection module 410 preferably comprises an electrode array 411 coupled to an electronics subsystem 412, wherein the electrode array 411 is configured to interface with the user, and the electronics system 412 is configured to condition, process, and/or transmit the set of signals for further analysis (e.g., using a wireless or wired interface). The biosignal detection module 410 can, however, comprise any other suitable element(s) or combination of element(s). Again, in some variations, the system 400 can substantially omit the biosignal detection module 410, such that modulation of the electrical stimulation treatment in is based upon a phase of a task of the set of tasks, or the user's performance of a phase of a task of the set of tasks, without consideration of a neurological state of the user detected by the biosignal detection module 410.

The processing subsystem 420 is configured to couple to the biosignal detection module 410, and functions to generate analyses that can be used to automatically synchronize a provided electrical stimulation treatment with a neurological signature. As such, the processing subsystem 420 can comprise a first module 422 configured to receive the signal stream, a second module 424 configured to identify a set of neurological signatures corresponding to each task of the set of tasks, based upon the signal stream (as described in relation to Block S140 above), and a third module 426 configured to generate a set of comparisons between a set of neurological metrics derived from the set of neurological signatures and at least one condition (as described in relation to Block S150 above). The processing subsystem 420 can comprise a transmission module (e.g., wireless transmission module, wired transmission module) configured to receive and/or transmit signals or analysis to/from a mobile device, other computing device, and/or data storage unit. The processing subsystem 420 can additionally comprise any other suitable element(s) or combination of element(s) configured to facilitate processing and/or transmission of data and analyses.

The electrical stimulation module 430 is preferably coupled to the controller 440, and functions to transmit an electrical stimulation treatment to the user in order to improve a neurological state of the user. The electrical stimulation module 430 is preferably configured to generate and provide TES treatments, but can additionally or alternatively be configured to provide any other suitable electrical stimulation treatment (e.g., PNS treatment). Preferably, the electrical stimulation module 430 comprises an electrode array 431 coupled to the controller 440, wherein the electrode array can be the same electrode array 411 of the biosignal detection module 410, or a second electrode array. The electrode array(s) of the electrical stimulation module 430 can be incorporated in a form factor comprising at least one of a head unit (e.g., for TES treatments) and an extremity unit (e.g., for PNS treatments), but can additionally or alternatively be incorporated in any other suitable form factor. In an example, the extremity unit can take the form of a band that couples to an extremity of the user, and incorporates a PNS stimulation unit, an accelerometer, and a transmission module (e.g., Bluetooth link) to track and report data describing movement. Furthermore, the electrical stimulation module 430 preferably comprises or is coupled to an electronics subsystem, which can be the same electronics subsystem of the biosignal detection module 410, or a second electronics subsystem. In some embodiments, the electrical stimulation module 430 can comprise an embodiment of the system for electrical stimulation described in U.S. application Ser. No. 14/470,683, entitled "Electrode System for Electrical Stimulation and Biosignal Detection" and filed on 27 Aug. 2014, which is herein incorporated in its entirety by this reference; however, the electrical stimulation module 430 can additionally or alternatively comprise any other suitable stimulation system.

The controller 440 preferably interfaces with the processor 420 and the electrical stimulation module 430, and functions to control provision and modulation of the electrical stimulation treatment based upon the set of comparisons. The controller 440 preferably also functions to cooperate with the processing subsystem 420 to maintain a parameter of the electrical stimulation treatment provided below a maximum limit. However, in some variations, the method 100 can substantially omit modulating the electrical stimulation treatment, by the processor 420 and the controller 440, according to a maximum limit constraint, such that modulation is based solely upon a task, a stage of a task and/or a detected neurological state of the user, without a maximum limit constraint. The controller can be coupled to the electronics subsystem of the electrical stimulation module 430, and can additionally be coupled to or comprise a stimulus generator configured to generate the electrical stimulation treatment (e.g., as a current generator, as a voltage generator, as a pulse generator, etc.). The stimulus generator is preferably configured to facilitate transmission of transcranial electrical stimulation (TES) in the form of at least one of: transcranial direct current stimulation (tDCS), transcranial alternating current stimulation (tACS), transcranial magnetic stimulation (TMS), transcranial random noise stimulation (tRNS), and transcranial variable frequency stimulation (tVFS). However, the stimulus generator can alternatively be configured to facilitate transmission of any other suitable stimulation to the user. Furthermore, the controller 440 can comprise or couple to any other suitable element that enables provision and modulation of an electrical stimulation treatment for the user based upon the user's interactions with the set of provided tasks.

The methods 100, 200, 300 and system 400 of the preferred embodiment and variations thereof can be embodied and/or implemented at least in part as a machine configured to receive a computer-readable medium storing computer-readable instructions. The instructions are preferably executed by computer-executable components preferably integrated with the system 200 and one or more portions of the processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of neuromodulation will recognize from the previous detailed description and from the figures and claims, modifications and changes can be made to the preferred embodiments of the invention without departing from the scope of this invention defined in the following claims.

We claim:
1. A method for providing electrical stimulation to a user at an electrical stimulation device, the method comprising:
at a processing system coupled to the electrical stimulation device:
determining a task;
determining a user progress level associated with the task;
determining an electrical stimulation treatment based on the task and the user progress level;
at the electrical stimulation device, providing the electrical stimulation treatment to a brain region of the user;

guiding the user in performing the task at a mobile computing device associated with the user, the mobile computing device coupled to the processing system;

recording a user performance metric during the task of interest;

modulating the electrical stimulation treatment based on the user performance metric; and updating the user progress level based on the modulated electrical stimulation treatment.

2. The method of claim 1, further comprising determining a second task based on the updated user progress level.

3. The method of claim 1, wherein providing the electrical stimulation treatment to a brain region of the user comprises providing the electrical stimulation treatment to a frontal lobe region of the user.

4. The method of claim 1, wherein determining the task comprises receiving input from the user at an application executing on the mobile computing device.

5. The method of claim 1, wherein the task comprises a cognitive task.

6. The method of claim 5, wherein the cognitive task comprises a questionnaire configured to assess a user's learning in relation to a predetermined desired skill.

7. The method of claim 1, wherein modulating the electrical stimulation treatment comprises altering a current amplitude of the electrical stimulation treatment.

8. The method of claim 1, further comprising tracking a progress level of the user, wherein the task is determined based on the progress level, and wherein the progress level is updated based on the performance metric.

9. The method of claim 1, further comprising selecting a second task based on the user performance metric.

10. A method for providing electrical stimulation to a user, the method comprising:

providing an electrical stimulation device at a surface of a head region of the user;

at a processing system coupled to the electrical stimulation device, determining a task of interest to the user;

with the electrical stimulation device, providing an electrical stimulation session, the electrical stimulation session having a set of portions, to a brain region of the user, wherein providing the electrical stimulation session comprises delivering a first portion of the set of portions of the electrical stimulation session to the brain region of the user, wherein the first portion is determined based on a task of interest to the user;

guiding the user in performing the task of interest at a mobile computing device associated with the user, the mobile computing device coupled to the processing system;

determining, at the processing system, a performance metric associated with the task of interest; and delivering a second portion of the set of portions of the electrical stimulation session based on the performance metric.

11. The method of claim 10, further comprising determining a second task based on the performance metric.

12. The method of claim 11, further comprising providing a second electrical stimulation session based on the second task.

13. The method of claim 10, wherein determining the task of interest to the user comprises receiving input from the user at an application executing on the mobile computing device.

14. The method of claim 10, wherein the task of interest is configured to increase a memory aptitude of the user.

15. The method of claim 14, wherein the task of interest comprises a game configured to test a user's working memory.

16. The method of claim 10, wherein modulating the electrical stimulation treatment comprises altering a current amplitude of the electrical stimulation treatment.

17. The method of claim 10, further comprising tracking a progress level of the user, wherein the task of interest is determined based on the progress level, and wherein the progress level is updated based on the performance metric.

18. The method of claim 10, further comprising modifying the task of interest based on the user performance metric.

19. The method of claim 10, wherein providing the electrical stimulation treatment to a brain region of the user comprises providing the electrical stimulation treatment to a frontal lobe region of the user.

* * * * *